United States Patent
Imai et al.

(10) Patent No.: US 8,263,972 B2
(45) Date of Patent: *Sep. 11, 2012

(54) ORGANIC ELECTROLUMINESCENT DEVICE AND DISPLAY MEDIUM

(75) Inventors: Akira Imai, Kanagawa (JP); Koji Horiba, Kanagawa (JP); Hidekazu Hirose, Kanagawa (JP); Takeshi Agata, Kanagawa (JP); Katsuhiro Sato, Kanagawa (JP)

(73) Assignee: Fuji Xerox Co. Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/623,116

(22) Filed: Nov. 20, 2009

(65) Prior Publication Data

US 2010/0276672 A1   Nov. 4, 2010

(30) Foreign Application Priority Data

Apr. 30, 2009   (JP) .................. 2009-110982

(51) Int. Cl.
H01L 35/24    (2006.01)
(52) U.S. Cl. ............. 257/40; 257/79; 257/83; 257/88; 257/98; 257/E51.001
(58) Field of Classification Search .......... 257/40, 257/79, 83, 88, 98
See application file for complete search history.

(56) References Cited

U.S. PATENT DOCUMENTS 4,539,507 A    9/1985 VanSlyke et al.
(Continued)

FOREIGN PATENT DOCUMENTS

JP    A 59-194393    11/1984
(Continued)

OTHER PUBLICATIONS

Vincett et al., "Electrical conduction and low voltage blue electroluminescence in vacuum-deposited organic films," *Thin Solid Films*, vol. 94, 1982, pp. 171-183.

(Continued)

*Primary Examiner* — Wai Sing Louie
(74) *Attorney, Agent, or Firm* — Oliff & Berridge, PLC

(57) ABSTRACT

An organic electroluminescent device includes: a pair of electrodes including a positive electrode and a negative electrode, at least one of the electrodes being transparent or semi-transparent; and an organic compound layer including one or more layers interposed between the pair of electrodes, at least one layer included in the organic compound layer containing one or more compounds represented by the following formula (I):

(I)

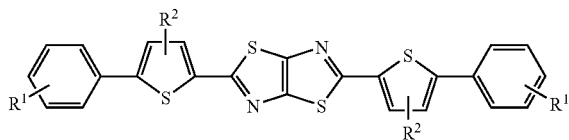

in formula (I), $R^1$s each independently representing a linear alkyl, linear alkoxy, branched alkyl, or branched alkoxy group having from 3 to 20 carbon atoms; and $R^2$s each independently representing a hydrogen atom, a linear alkyl group having from 1 to 20 carbon atoms, a linear alkoxy group having from 1 to 20 carbon atoms, a branched alkyl group having from 3 to 20 carbon atoms, or a branched alkoxy group having from 3 to 20 carbon atoms.

19 Claims, 1 Drawing Sheet

U.S. PATENT DOCUMENTS

| | | | |
|---|---|---|---|
| 5,247,190 | A | 9/1993 | Friend et al. |
| 5,399,502 | A | 3/1995 | Friend et al. |
| 5,574,291 | A | 11/1996 | Dodabalapur et al. |
| 5,596,208 | A | 1/1997 | Dodabalapur et al. |
| 5,659,181 | A | 8/1997 | Bridenbaugh et al. |
| 5,946,551 | A | 8/1999 | Dimitrakopoulos et al. |
| 5,981,970 | A | 11/1999 | Dimitrakopoulos et al. |
| 6,107,117 | A | 8/2000 | Bao et al. |
| 2010/0209630 | A1* | 8/2010 | Watanabe et al. ............ 428/1.31 |
| 2010/0236631 | A1* | 9/2010 | Kiselev et al. ................ 136/263 |
| 2010/0243995 | A1* | 9/2010 | Horiba et al. ................... 257/40 |

FOREIGN PATENT DOCUMENTS

| | | |
|---|---|---|
| JP | A-05-055568 | 3/1993 |
| JP | A-05-190877 | 7/1993 |
| JP | A-08-228034 | 9/1996 |
| JP | A-08-228035 | 9/1996 |
| JP | A-08-264805 | 10/1996 |
| JP | A 10-92576 | 4/1998 |
| JP | A-10-125924 | 5/1998 |
| JP | A 10-168443 | 6/1998 |
| JP | A-10-190001 | 7/1998 |
| JP | A-10-270712 | 10/1998 |
| JP | A-2000-174277 | 6/2000 |
| JP | A-2001-094107 | 4/2001 |
| JP | A 2006-206503 | 8/2006 |
| JP | A-2006-206503 | 8/2006 |
| JP | A 2008-239987 | 10/2008 |

OTHER PUBLICATIONS

Tang et al., "Organic electroluminescent diodes," Appl. Phys. Lett., vol. 51, No. 12, Sep. 21, 1987, pp. 913-915.

Wakamoto et al., "Organic Electroluminescence Devices with a Starburst Amine as a Hole Transport Material," *The 40th Meeting, Japan Society of Applied Physics & Related Societies*, 30a-SZK-14, 1993.

Ando et al., "Synthesis, physical properties, and field-effect transistors of novel thiophene/thiazolothiazole co-oligomers," *Journal of Materials Chemistry*, vol. 14, 2004, pp. 1787-1790.

Ando et al., "Characterization and Field-Effect Transistor Performance of Heterocyclic Oligomers Containing a Thiazolothiazole Unit," *Chemistry Letters*, vol. 33, No. 9, 2004, pp. 1170-1171.

Johnson et al., "Thiazolothiazoles. II. The Parent Heterocycle and Its Carboxylic and Amino Derivatives," *Journal of the American Chemical Society*, vol. 92, No. 13, Jul. 1, 1970, pp. 4046-4050.

Drury et al., "Low-cost all-polymer integrated circuits," *Applied Physics Letters*, 1998, vol. 73, No. 1, pp. 108-110.

Ando et al., "Synthesis, physical properties, and field-effect transistors of novel thiophene/thiazolothiazole co-oligomers," *J. Mater. Chem.*, 2004, vol. 14, pp. 1787-1790.

Ando et al., "Characterization and Field-Effect Transistor Performance of Heterocyclic Oligomers Containing a Thiazolothiazole Unit," *Chemistry Letters*, 2004, vol. 33, No. 9, pp. 1170-1171.

Johnson et al., "Thiazolothiazoles. II. Parent heterocycle and its carboxylic and amino derivatives," *J. Am. Chem. Soc.*, 1970, vol. 92, No. 13, pp. 4046-4050.

Ando et al., "High Performance n-Type Organic Field-Effect Transistors Based on π-Electronic Systems with Trifluoromethylphenyl Groups," *J. Am. Chem. Soc.*, 2005, vol. 127, pp. 5336-5337.

Japanese Office Action in Japanese Patent Application No. 2009-072222; dated Aug. 23, 2011 (with English-language translation).

Mamada et al., "Preparation, Characterization, and Field-effect Transistor Performance of Benzo[1,2-d:4,5-d']bisthiazole Derivatives," Chemistry Letters, vol. 37, No. 7, 2008, pp. 766-767.

Kumaki et al., "Significant improvement of electron mobility in organic thin-film transistors based on thiazolothiazole derivative by employing self-assembled monolayer," Applied Physics Letters, 90, 053506, 2007, pp. 053506-1-053506-3.

Nov. 28, 2011 Notice of Allowance issued in U.S. Appl. No. 12/558,904.

* cited by examiner

ORGANIC ELECTROLUMINESCENT DEVICE AND DISPLAY MEDIUM

CROSS-REFERENCE TO RELATED APPLICATIONS

This application is based on and claims priority under 35 USC 119 from Japanese Patent Application No. 2009-110982 filed Apr. 30, 2009.

BACKGROUND

1. Technical Field

The present invention relates to an organic electroluminescent device, and a display medium.

2. Related Art

Electroluminescent devices are self-luminescent, all-solid devices, and since they exhibit high visibility and are strong against impact, the electroluminescent devices are expected to be utilized in a broad range of applications. Currently, electroluminescent devices making use of inorganic fluorescent materials constitute the mainstream, and are widely used.

Meanwhile, studies on electroluminescent devices utilizing organic compounds were started initially by using single crystals of anthracene or the like, and now there are attempts to process such organic compounds into thin films based on deposition methods (see, for example, Thin Solid Films, 94, 171 (1982)). The light emission of these devices is a phenomenon in which, when electrons are injected from one of the electrodes, and holes are injected from the other electrode, the luminescent material in the electroluminescent device is excited to a higher energy level, and the excess energy generated when the excited luminescent body returns to the ground state, is emitted as light.

SUMMARY

According to an aspect of the invention, there is provided an organic electroluminescent device including:

a pair of electrodes including a positive electrode and a negative electrode, at least one of the electrodes being transparent or semi-transparent; and an organic compound layer including one or more layers interposed between the pair of electrodes, at least one layer included in the organic compound layer containing one or more compounds represented by the following formula (I):

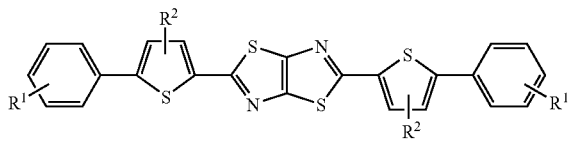

(I)

in formula (I), $R^1$s each independently representing a linear alkyl group having from 3 to 20 carbon atoms, a linear alkoxy group having from 3 to 20 carbon atoms, a branched alkyl group having from 3 to 20 carbon atoms, or a branched alkoxy group having from 3 to 20 carbon atoms; and $R^2$s each independently representing a hydrogen atom, a linear alkyl group having from 1 to 20 carbon atoms, a linear alkoxy group having from 1 to 20 carbon atoms, a branched alkyl group having from 3 to 20 carbon atoms, or a branched alkoxy group having from 3 to 20 carbon atoms.

BRIEF DESCRIPTION OF THE DRAWINGS

Exemplary embodiments of the present invention will be described in detail based on the following figures, wherein.

DETAILED DESCRIPTION

Figure 1:
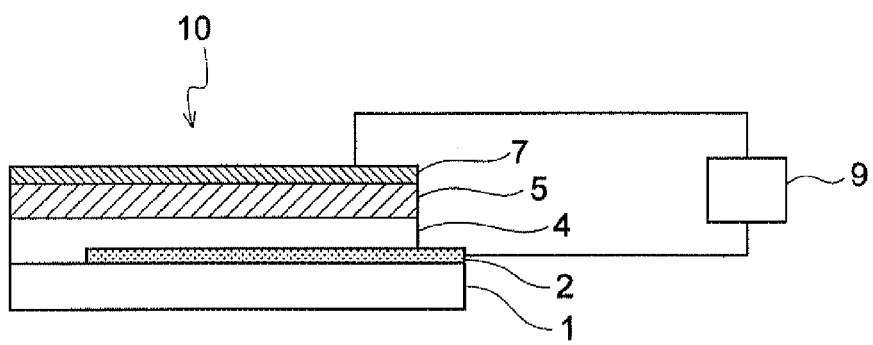
FIG. 1 is a schematic configuration diagram showing a display device according to an exemplary embodiment of the invention.

First, the organic electroluminescent device according to an exemplary embodiment of the invention will be explained in detail.

The organic electroluminescent device according to the exemplary embodiment includes: a pair of electrodes including a positive electrode and a negative electrode, at least one of the electrodes being transparent or semi-transparent; and an organic compound layer including one or more layers interposed between the pair of electrodes. At least one layer included in the organic compound layer contains one or more compounds represented by the following formula (I).

The organic electroluminescent device according to the exemplary embodiment of the invention has a long device lifespan due to the configuration as described above. First, the compound represented by the following formula (I) will be described in detail.

The compound represented by formula (I) is a thiazolothiazole compound. Hereinafter, the compound represented by formula (I) may also be referred to as a thiazolothiazole compound represented by formula (I).

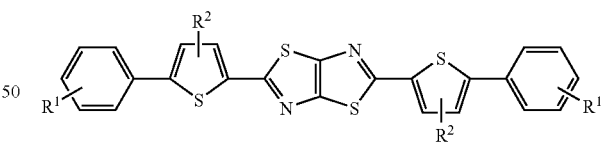

(I)

In formula (I), $R^1$s each independently represent a linear alkyl group having from 3 to 20 carbon atoms, a linear alkoxy group having from 3 to 20 carbon atoms, a branched alkyl group having from 3 to 20 carbon atoms, or a branched alkoxy group having from 3 to 20 carbon atoms; and $R^2$s each independently represent a hydrogen atom, a linear alkyl group having from 1 to 20 carbon atoms, a linear alkoxy group having from 1 to 20 carbon atoms, a branched alkyl group having from 3 to 20 carbon atoms, or a branched alkoxy group having from 3 to 20 carbon atoms.

Among them, an embodiment in which $R^1$ in formula (I) is a linear substituent having from 3 to 12 carbon atoms, or a branched substituent having from 3 to 12 main chain carbon atoms, and $R^2$ is a linear substituent having from 1 to 12 carbon atoms, or a branched substituent having from 2 to 12 main chain carbon atoms may be exemplified.

Here, the linear substituent having from 3 to 12 carbon atoms may be a linear alkyl group having from 3 to 12 carbon atoms, or a linear alkoxy group having from 3 to 12 carbon atoms. The branched substituent having from 3 to 12 main chain carbon atoms may be a branched alkyl or alkoxy group having from 3 to 20 carbon atoms in which the linear main chain moiety of the alkyl or alkoxy group (excluding branching chains) has from 2 to 12 carbon atoms.

The thiazolothiazole compound represented by formula (I) is thought to be able to exhibit excellent charge transportability due to its high planarity of the aromatic rings and extended conjugation of π electrons in view of the molecular structure.

The thiazolothiazole compound represented by formula (I) has improved solubility because a phenyl group is introduced as the substituent adjacent to the thiophene ring. It is speculated that this is because the bond between the terminal phenyl substituent and the thiophene ring is capable of rotating freely. Furthermore, it is thought that since an alkyl group or an alkoxy group is introduced into $R^1$, the hydrophobic interaction of the compound with organic solvents is increased, and thus the solubility in organic solvents is enhanced. It is also thought that since an alkyl group or an alkoxy group is further introduced into $R^2$, the hydrophobic interaction of the compound with organic solvents is increased, and thus the solubility is enhanced to a large extent. These substitutions also have an effect of lowering the ionization potential. It is also speculated that since an alkyl group or an alkoxy group is introduced as a substituent for the phenyl group, the molecular weight is increased, and the compound exhibits good thermal resistance.

In particular, it is thought that in the thiazolothiazole compound represented by formula (I), because the length of the substituents $R^1$ and $R^2$ is restricted to an alkyl group or alkoxy group having 20 or less carbon atoms, or 12 or less carbon atoms (or 8 or less carbon atoms for $R^2$), entanglement of the substituents is suppressed, which also contributes to the enhancement of solubility.

Here, the thiazolothiazole compound represented by the following chemical formula 3, which does not belong to the thiazolothiazole compound family represented by formula (I), may be obtained as crystals; however, since it is difficult to dissolve the compound in organic solvents, when the compound is used to prepare a coating solution, crystals are precipitated out, and thus the coating solution is poor in stability over time and is difficult to use. Furthermore, when the thiazolothiazole compound represented by the chemical formula 3 is used to form films, there occurs unevenness in the film thickness; in contrast, when a thiazolothiazole compound represented by formula (I) is used in film formation, the occurrence of unevenness in the coating film thickness is suppressed.

Chemical Formula 3

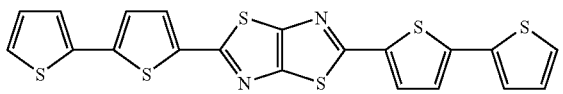

Therefore, an organic electroluminescent device that includes a thiazolothiazole compound represented by formula (I) having the specific structure as described above in at least one layer included in the organic compound layer is thought to have an extended lifespan. However, the present exemplary embodiment is not limited by the supposition described above.

Hereinafter, the thiazolothiazole compound represented by formula (I) will be explained in detail.

The linear alkyl group having from 3 to 20 carbon atoms for $R^1$ may be specifically a propyl group, a butyl group, a hexyl group, an octyl group, a decyl group, a dodecyl group, a tetradecyl group, a hexadecyl group, an octadecyl group, or an icosyl group, and more specifically a linear alkyl group having from 3 to 12 carbon atoms. Specific examples thereof include a propyl group, a butyl group, a hexyl group, an octyl group, a decyl group, and a dodecyl group, and more specific examples include a butyl group, a hexyl group, an n-octyl group, and a dodecyl group.

The linear alkoxy group having from 3 to 20 carbon atoms for $R^1$ may be specifically a methoxy group, an ethoxy group, a propoxy group, a butoxy group, a hexyloxy group, an octyloxy group, a decyloxy group, a dodecyloxy group, a tetradecyloxy group, a hexadecyloxy group, an octadecyloxy group, or an icosyloxy group, and more specifically a linear alkoxy group having from 3 to 12 carbon atoms. Specific examples thereof include a propoxy group, a butoxy group, a hexyloxy group, an octoxy group, an octyloxy group, a decyloxy group, and a dodecyloxy group, and more specific examples include a butoxy group, a hexyloxy group, an octoxy group, and a dodecyloxy group.

The branched alkyl group having from 3 to 20 carbon atoms for $R^1$ may be specifically an isopropyl group, an isobutyl group, a sec-butyl group, a tert-butyl group, an isopentyl group, a tert-pentyl group, a 1-methylpentyl group, a 4-methylpentyl group, a 3,3-dimethylbutyl group, a 2-ethylbutyl group, a 1-methylhexyl group, a tert-octyl group, a 1-methylheptyl group, a 2-ethylhexyl group, a 2-propylpentyl group, a 2,2-dimethylhexyl group, a 2-methyloctyl group, a 2,2-dimethylheptyl group, a 2,2-dimethyloctyl group, a 2,3-dimethyloctyl group, a 2,6-dimethyl-4-heptyl group, a 3,5,5-trimethylhexyl group, a 1-methyldecyl group, a 2-methyldecyl group, a 2,2-dimethyldecyl group, a 2,3-dimethyldecyl group, a 2,2-diethyldecyl group, a 1-hexylheptyl group, a 1-methylhexadecyl group, or a 1,1-dimethylhexadecyl group, and more specifically a branched alkyl group having from 3 to 12 carbon atoms. Specific examples thereof include an isopropyl group, a tert-butyl group, a 2-methylhexyl group, a 2,2-dimethylhexyl group, a 2-methyloctyl group, a 2,2-dimethyloctyl group, a 2,3-dimethyloctyl group, a 2-methyldecyl group, a 2,2-dimethyldecyl group, and a 2,3-dimethyldecyl group, and more specific examples include a tert-butyl group, a 2,2-dimethylhexyl group, a 2-methyloctyl group, a 2,2-dimethyloctyl group, a 2,3-dimethyloctyl group, and a 2,2-dimethyldecyl group.

The branched alkoxy group having from 3 to 20 carbon atoms for $R^1$ may be specifically an isopropoxy group, an isobutoxy group, a sec-butoxy group, a tert-butoxy group, a 3,3-dimethylbutyloxy group, a 2-ethylbutyloxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2-dimethyldecyloxy group, a 2,3-dimethyldecyloxy group, a 2-methyldodecyloxy group, a 2-methyltetradecyloxy group, a 2-methylhexadecyloxy group, or a 2-methyloetadecyloxy group, and more specifically a branched alkoxy group having from 3 to 12 carbon atoms. Specific examples thereof include an isopropoxy group, a tert-butoxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2- dimethyldecyloxy group, and a 2,3-dimethyldecyloxy group, and more specific examples include a tert-butoxy group, a 2-methyloctyloxy group, a 2,2-dimethyloctyloxy group, and a 2,3-dimethyldecyloxy group.

The bonding position for $R^1$ in the phenyl group may be specifically the 3-position or the 4-position with respect to the thiophene ring, and more specifically the 4-position. The alkyl group or alkoxy group for $R^1$ may have substituents, and the alkyl group or alkoxy group may not have substituents.

Furthermore, the linear alkyl group having from 1 to 20 carbon atoms for $R^2$ may be specifically a methyl group, an ethyl group, a propyl group, a butyl group, a hexyl group, an octyl group, a decyl group, a dodecyl group, a tetradecyl group, a hexadecyl group, an octadecyl group, or an icosyl group, and more specifically a linear alkyl group having from 1 to 8 carbon atoms. Specific examples thereof include a methyl group, an ethyl group, a propyl group, a butyl group, a hexyl group, and an octyl group, and more specific examples include a methyl group, a butyl group, a hexyl group, and an octyl group. More specifically, the linear alkyl group for $R^2$ may be a linear alkyl group having from 3 to 8 carbon atoms, and still more specifically a propyl group, a butyl group, a hexyl group, or an octyl group.

The linear alkoxy group having from 1 to 20 carbon atoms for $R^2$ may be specifically a methoxy group, an ethoxy group, a propoxy group, a butoxy group, a hexyloxy group, an octyloxy group, a decyloxy group, a dodecyloxy group, a tetradecyloxy group, a hexadecyloxy group, an octadecyloxy group, or an icosyloxy group, and more specifically a linear alkoxy group having from 1 to 8 carbon atoms. Specific examples thereof include a methoxy group, an ethoxy group, a propoxy group, a butoxy group, a hexyloxy group, and an octyloxy group, and more specific examples include a methoxy group, a butoxy group, and a hexyloxy group. More specifically, the linear alkoxy group for $R^2$ may be a linear alkoxy group having from 3 to 8 carbon atoms, and still more specifically a butoxy group or a hexyloxy group.

The branched alkyl group having from 3 to 20 carbon atoms for $R^2$ may be specifically an isopropyl group, an isobutyl group, a sec-butyl group, a tert-butyl group, an isopentyl group, a tert-pentyl group, a 1-methylpentyl group, a 4-methylpentyl group, a 3,3-dimethylbutyl group, a 2-ethylbutyl group, a 1-methylhexyl group, a tert-octyl group, a 1-methylheptyl group, a 2-ethylhexyl group, a 2-propylpentyl group, a 2,2-dimethylhexyl group, a 2-methyloctyl group, a 2,2-dimethylheptyl group, a 2,2-dimethyloctyl group, a 2,3-dimethyloctyl group, a 2,6-dimethyl-4-heptyl group, a 3,5,5-trimethylhexyl group, a 1-methyldecyl group, a 2-methyldecyl group, a 2,2-dimethyldecyl group, a 2,3-dimethyldecyl group, a 2,2-diethyldecyl group, a 1-hexylheptyl group, a 1-methylhexadecyl group, or a 1,1-dimethylhexadecyl group, and more specifically a branched alkyl group having from 3 to 12 carbon atoms. Specific examples thereof include an isopropyl group, a tert-butyl group, a 2-methylhexyl group, a 2,2-dimethylhexyl group, a 2-methyloctyl group, a 2,2-dimethyloctyl group, a 2,3-dimethyloctyl group, a 2-methyldecyl group, a 2,2-dimethyldecyl group, and a 2,3-diemethyldecyl group, and more specific examples include a tert-butyl group, a 2,2-dimethylhexyl group, a 2-methyloctyl group, a 2,2-dimethyloctyl group, a 2,3-dimethyloctyl group, and a 2,2-dimethyldecyl group. More specifically, the branched alkyl group for $R^2$ may be a branched alkyl group having from 3 to 8 carbon atoms, and still more specifically a tert-butyl group, or a 2,2-dimethylhexyl group.

The branched alkoxy group having from 3 to 20 carbon atoms for $R^2$ may be specifically an isopropoxy group, an isobutoxy group, a sec-butoxy group, a tert-butoxy group, a 3,3-dimethylbutyloxy group, a 2-ethylbutyloxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2-dimethyldecyloxy group, a 2,3-dimethyldecyloxy group, a 2-methyldodecyloxy group, a 2-methyl etradecyloxy group, a 2-methylhexadecyloxy group, or a 2-methyloctadecyloxy group, and more specifically a branched alkoxy group having from 3 to 12 carbon atoms. Specific examples thereof include an isopropoxy group, a tert-butoxy group, a 2-methylhexyloxy group, a 2,2-dimethylhexyloxy group, a 2-methyloctyloxy group, a 2,2-dimethyloctyloxy group, a 2,3-dimethyloctyloxy group, a 2-methyldecyloxy group, a 2,2-dimethyldecyloxy group, and a 2,3-dimethyldecyloxy group, and more specific examples include a tert-butoxy group, a 2-methyloctyloxy group, a 2,2-dimethyloctyloxy group, and a 2,3-dimethyldecyloxy group. More specifically, the branched alkoxy group for $R^2$ may be a branched alkoxy group having from 3 to 8 carbon atoms, and still more specifically a tert-butoxy group or an isopropoxy group.

The bonding position for $R^2$ in the thiophene ring may be specifically the 3-position with respect to the phenyl group. The alkyl group or alkoxy group for $R^2$ may have substituents, and the alkyl group or alkoxy group may not have substituents.

In particular, $R^1$ in formula (I) may be a linear alkyl group having from 3 to 20 carbon atoms, a linear alkoxy group having from 3 to 20 carbon atoms, a branched alkyl group having from 3 to 20 carbon atoms, or a branched alkoxy group having from 3 to 20 carbon atoms, and $R^2$ may be a linear alkyl group having from 3 to 8 carbon atoms, a linear alkoxy group having from 3 to 8 carbon atoms, a branched alkyl group having from 3 to 8 carbon atoms, or a branched alkoxy group having from 3 to 8 carbon atoms. In this case, the compound has good solubility in halogen organic solvents as well as in non-halogen organic solvents.

The production of a thiazolothiazole compound having the above-described structure is easily achieved, and the purification thereof is easily achieved so that a high purity product is easily obtained, and it is easy to produce, for example, a charge transporting material using the thiazolothiazole compound having the above-described structure.

The term "dissolved" as used in the exemplary embodiment refers to a state in which the presence of crystals may not be confirmed by visual inspection when a thiazolothiazole compound represented by formula (I) is added to an organic solvent. The phrase "solubility is good" indicates a state in which the compound has been dissolved at the boiling point of the organic solvent.

In regard to the organic solvent that dissolves the thiazolothiazole compound represented by formula (I), any kind may be used as long as it dissolves the thiazolothiazole compound represented by formula (I). For example, conventional organic solvents such as methanol, ethanol, 1-propanol, 2-propanol, 1-butanol, benzyl alcohol, methylcellosolve, ethylcellosolve, acetone, methyl ethyl ketone, cyclohexanone, methyl acetate, n-butyl acetate, dioxane, tetrahydrofuran, diethyl ether, toluene, xylene, mesitylene, N,N-dimethylformamide, N,N-dimethylacetamide, and dimethylsulfoxide, or the following halogenated organic solvents may be used singly or as a mixture of two or more species.

The halogenated organic solvents may be hydrocarbon compounds and aromatic hydrocarbon compounds having one or more halogen atoms such as a fluorine atom, a chlorine atom, a bromine atom and an iodine atom, which may be solvents having a boiling point in the range of from 30° C. to 300° C. More specifically, the halogenated organic solvents may be hydrocarbon compounds and aromatic hydrocarbon compounds having one or more halogen atoms and having a boiling point in the range of from 50° C. to 200° C.

Specific examples of the halogenated organic solvents include halogenated hydrocarbons such as chloroform, carbon tetrachloride, 1,2-dichloroethane and 1,1,2-trichloroethane; halogenated aromatic hydrocarbons such as chlorobenzene, o-dichlorobenzene, 1,2,4-trichlorobenzene, 2-chlorotoluene and 2,4-dichlorotoluene; and the like.

The thiazolothiazole compound represented by formula (I) is, for example, synthesized as described below, but the method of synthesis is not intended to be limited to these.

(1) The thiazolothiazole compound is synthesized by halogenating the 5-positions of the thiophenes adjacent to the thiazolothiazole site, and then performing a Suzuki reaction of an alkyl group- or alkoxy group-substituted phenyl boronic acid or boronic acid ester (such as boronic acid pinacol ester) with the aforementioned halogenated compound.

(2) The thiazolothiazole compound is synthesized by performing a Suzuki reaction of an alkyl group- or alkoxy group-substituted phenyl bromide with a thiophene boronic acid to synthesize an alkyl group- or alkoxy group-substituted phenyl thiophene, subsequently formylating the 5-position of the thiophene in the alkyl group- or alkoxy group-substituted phenyl thiophene, and then performing a cyclization reaction with rubeanic acid or the like.

The synthesis method of (2) is a method described in, for example, JP-A No. 2006-206503, the disclosure of which is incorporated by reference herein. On the other hand, the synthesis method of (1) includes, for example, forming a thiophene-containing thiazolothiazole skeleton, subsequently halogenating the 5-positions of the thiophenes, and introducing terminal substituents through a Suzuki reaction with an alkyl- or alkoxy-phenyl boronic acid or boronic acid ester (such as boronic acid pinacol ester), in which purification is carried out in the respective steps.

The method for producing the thiazolothiazole compound will be explained specifically. In the exemplary embodiment, the thiazolothiazole compound [formula (I)] is synthesized by performing a cyclization reaction of rubeanic acid and a thiophenaldehyde compound represented by the following formula (II-1) to synthesize a thiophene-containing thiazolothiazole [formula (III-1) shown below] as described in, for example, J. R. Johnson, D. H. Rotenberg, and R. Ketcham, J. Am. Chem., Soc., Vol. 92, 4046 (1970), subsequently halogenating the product with N-bromosuccinimide (hereinafter, referred to as NBS), which is a known method, to synthesize a halogen compound represented by the following formula (IV-1), and subjecting this halogen compound to a coupling reaction through a Suzuki reaction using a substituted phenyl boronic acid or substituted phenyl boronic acid ester (such as boronic acid pinacol ester) represented by the following formula (V-1) and a palladium catalyst.

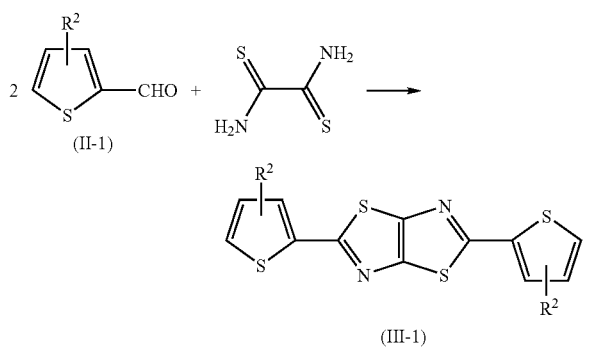

(II-1)

(III-1)

Both $R^2$ in formula (II-1) and $R^2$ in formula (III-1) have the same meanings as defined for $R^2$ in formula (I).

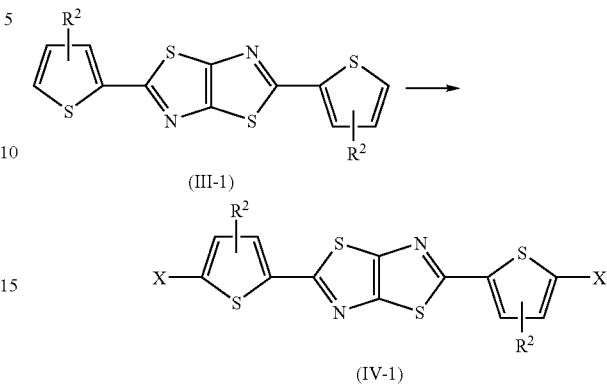

(III-1)

(IV-1)

In formula (IV-1), $R^2$ has the same meaning as defined for $R^2$ in formula (I). X represents a bromine atom or an iodine atom.

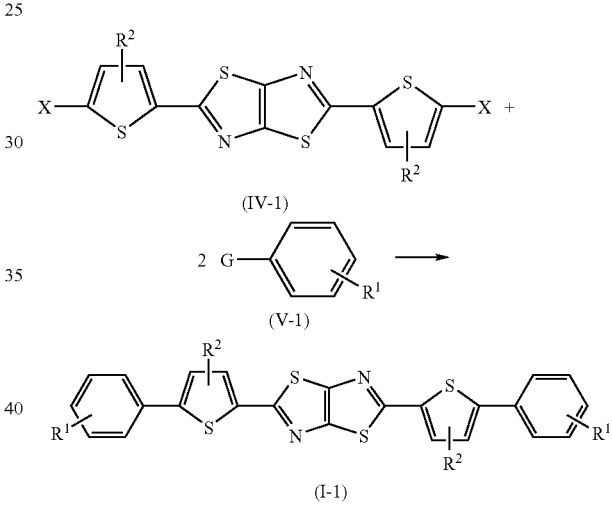

(IV-1)

(V-1)

(I-1)

In formula (V-1), $R^1$ has the same meaning as defined for $R^1$ in formula (I). G represents a boronic acid group or a boronic acid ester group.

As for the boronic acid ester group, for example, those shown below may be used from the viewpoint of availability of the reagent.

Specific examples of the boronic acid ester group include a boronic acid pinacol ester group, a boronic acid 1,3-propanediol ester group, and a boronic acid neopentyl glycol ester group.

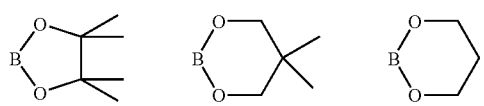

Specific compounds of the thiazolothiazole compound represented by formula (I) will be presented below, but the thiazolothiazole compound is not intended to be limited to these.

| No. | R¹ | R¹ binding position | R² | R² binding position |
|---|---|---|---|---|
| 1 | CH₂CH₂CH₂CH₃ | 4 | —H | 3 |
| 2 | CH₂CH₂CH₂CH₂CH₃ | 4 | —H | 3 |
| 3 | CH₂(CH₂)₄CH₃ | 4 | —H | 3 |
| 4 | CH₂(CH₂)₆CH₃ | 4 | —H | 3 |
| 5 | CH₂(CH₂)₁₀CH₃ | 4 | —H | 3 |
| 6 | CH₂CH₂CH₂CH₂CH₃ | 4 | —H | 3 |
| 7 | CH₂CH₂CH₂CH₂CH₃ | 4 | —CH₃ | 3 |
| 8 | CH₂(CH₂)₆CH₃ | 4 | —CH₃ | 3 |
| 9 | CH₂(CH₂)₁₀CH₃ | 4 | —CH₃ | 3 |
| 10 | —O—CH₃ | 4 | —O—CH₃ | 3 |
| 11 | —O—CH₂CH₃ | 4 | —H | 3 |
| 12 | —O—CH₂(CH₂)₃CH₃ | 4 | CH₂CH₂CH₂CH₂CH₃ | 3 |
| 13 | —O—CH₂(CH₂)₅CH₃ | 4 | —CH₃ | 3 |
| 14 | —O—CH₂(CH₂)₉CH₃ | 4 | CH₃CH(CH₂CH₂CH₃)CH₂— | 3 |
| 15 | —C(CH₃)₃ | 4 | —H | 3 |
| 16 | CH₃C(CH₃)(CH₂CH₂CH₃)— | 4 | CH₃CH(CH₂CH₃)— | 3 |

-continued
| No. | R¹ | R¹ binding position | R² | R² binding position |
|---|---|---|---|---|
| 17 | 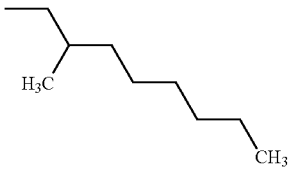 | 4 | 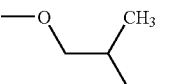 | 3 |
| 18 | 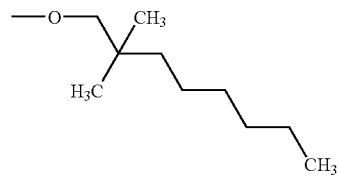 | 4 | 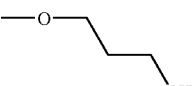 | 3 |
| 19 | 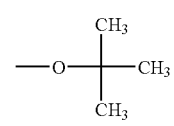 | 4 | 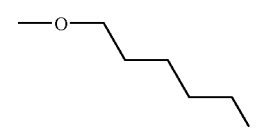 | 3 |
| 20 | 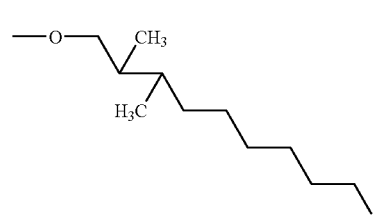 | 4 | —CH₃ | 3 |
| 21 | 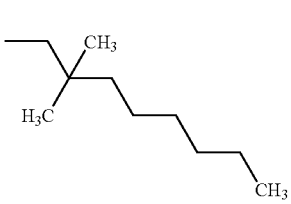 | 4 | —H | 3 |
| 22 | 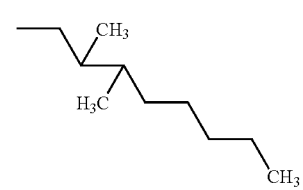 | 4 | 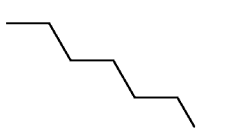 | 3 |
| 23 | 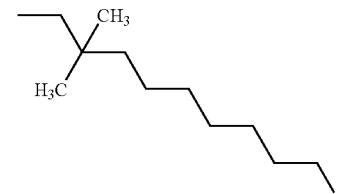 | 4 | —CH₃ | 3 |
| 24 | 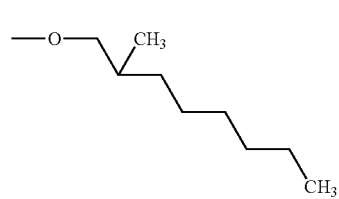 | 4 | 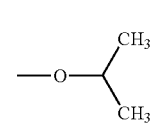 | 3 |

-continued

| No. | R¹ | R¹ binding position | R² | R² binding position |
|---|---|---|---|---|
| 25 | CH₃(CH₂)₄— (pentyl) | 4 | CH₃(CH₂)₇— (octyl) | 3 |
| 26 | CH₃(CH₂)₆— (heptyl) | 4 | CH₃(CH₂)₈— (nonyl) | 3 |
| 27 | CH₃(CH₂)₈— (nonyl) | 4 | CH₃(CH₂)₉— (decyl) | 3 |
| 28 | CH₃(CH₂)₁₂— (tridecyl) | 4 | CH₃(CH₂)₉— (decyl) | 3 |
| 29 | CH₃(CH₂)₂—O— (propoxy) | 4 | CH₃(CH₂)₉— (decyl) | 3 |
| 30 | CH₃(CH₂)₄—O— (pentyloxy) | 4 | CH₃(CH₂)₇— (octyl) | 3 |
| 31 | CH₃(CH₂)₆—O— (heptyloxy) | 4 | CH₃(CH₂)₇— (octyl) | 3 |
| 32 | CH₃(CH₂)₉—O— (decyloxy) | 4 | CH₃(CH₂)₇— (octyl) | 3 |
| 33 | CH₃(CH₂)₂—O— (propoxy) | 2 | CH₃(CH₂)₇— (octyl) | 3 |
| 34 | (CH₃)(C₂H₅)(n-C₄H₉)C— | 2 | CH₃(CH₂)₂—O— (propoxy) | 3 |
| 35 | CH₃(CH₂)₈— (nonyl) | 2 | (C₂H₅)₂CH— | 3 |
| 36 | CH₃(CH₂)₅CH(CH₃)CH₂—O— | 2 | —CH₃ | 3 |

-continued

| No. | R¹ | R¹ binding positoin | R² | R² binding position |
|-----|----|----|----|----|
| 37 | —O—CH₂—CH(CH₃)— (branched alkoxy) | 3 | —(CH₂)₆—CH₃ | 3 |
| 38 | —C(CH₃)₂—CH₂—CH₂—CH₃ | 3 | —O—CH₂—CH(CH₃)— | 3 |
| 39 | —(CH₂)₇—CH₃ | 3 | —CH₂—CH(CH₃)—CH₃ (isobutyl) | 3 |
| 40 | —O—CH₂—CH(CH₃)—(CH₂)₄—CH₃ | 3 | —CH₃ | 3 |

Next, the configuration of the organic electroluminescent device according to the exemplary embodiment will be described in detail.

The organic electroluminescent device according to the exemplary embodiment includes: a pair of electrodes including a positive electrode and a negative electrode, at least one of the electrodes being transparent or semi-transparent; and an organic compound layer including one or more layers interposed between the pair of electrodes. At least one layer included in the organic compound layer contains one or more thiazolothiazole compounds represented by formula (I).

The layer configuration in the organic electroluminescent device according to the exemplary embodiment is not particularly limited as long as the organic electroluminescent device has the configuration described above.

In the organic electroluminescent device of the exemplary embodiment, when the organic compound layer consists of a light emitting layer only, the organic compound layer means a light emitting layer having charge transport capability, and this light emitting layer having charge transport capability contains the thiazolothiazole compound represented by formula (I).

Here, if the organic compound layer consists of a light emitting layer, size enlargement and production of the electroluminescent device are easier as compared with other layer configurations. This is because the number of layers is small, and the layer is produced by, for example, wet type coating or the like.

The organic electroluminescent device of the exemplary embodiment may also be a device of so-called function separated type, in which the organic compound layer consists of plural layers, and each of the layers has a different function. In this case, at least one of the layers is a light emitting layer, and other layers may include charge transport layers, that is, a hole transport layer, an electron transport layer, or a hole transport layer and an electron transport layer. At least one layer among these contains the thiazolothiazole compound represented by formula (I). Here, the light emitting layer in a device of function separate type may be a light emitting layer having charge transport capability.

Regarding the specific configuration of the organic compound layer having a layer configuration that includes a light emitting layer or a light emitting layer having charge transport capability and other layers, the following (1) to (3) may be mentioned.

(1) Configuration including at least one light emitting layer, and at least one layer of an electron transport layer or an electron injection layer.

Here, in this layer configuration, a balance is achieved between the ease of production and luminescence efficiency, as compared with other layer configurations. It is speculated that this is because the number of layers is smaller than layer configurations having all functions separated, while the injection efficiency of electrons having lower mobility than holes in general is compensated, and balancing of charges in the light emitting layer is attempted.

(2) Configuration including at least one layer of a hole transport layer or a hole injection layer, at least one light emitting layer, and at least one layer of an electron transport layer or an electron injection layer.

Here, in this layer configuration, the luminescence efficiency is excellent as compared with devices of other layer configurations, and low voltage driving is realized. It is speculated that this is because the injection efficiency of charges is the maximum due to all functions being separated, as compared with other layer configurations, and the charges recombine at the light emitting layer.

(3) Configuration including at least one layer of a hole transport layer or a hole injection layer, and at least one light emitting layer.

Here, in this layer configuration, a balance between the ease of production and durability is achieved as compared with other configurations. It is speculated that this is because the number of layers is smaller compared with layer configurations having all functions separated, while the efficiency of hole injection to the light emitting layer is enhanced, and excess injection of electrons is suppressed at the light emitting layer.

So long as the thiazolothiazole compound represented by formula (I) is contained in at least any one of these layers (hole transport layer, electron transport layer, and light emitting layer), there is no particular limitation on the layer containing the thiazolothiazole compound represented by formula (I).

Specifically, the thiazolothiazole compound represented by formula (I) may be contained as a material for the hole transport layer.

In regard to the organic electroluminescent device according to the exemplary embodiment, the light emitting layer, the hole transport layer, the hole injection layer, the electron transport layer, and the electron injection layer may further contain other charge transporting compounds (hole transporting materials or electron transporting materials) in addition to the thiazolothiazole compound represented by formula (I). The details of these charge transporting compounds will be described later.

In the organic electroluminescent device of the exemplary embodiment, the light emitting layer, the hole transport layer, the hole injection layer, the electron transport layer and the electron injection layer may contain charge transporting compounds (hole transporting materials or electron transporting materials) other than the thiazolothiazole compound represented by formula (I). The details of these other charge transporting compounds will be described later.

Hereinafter, the organic electroluminescent device of the exemplary embodiment will be explained in more detail while referring to the drawings, but the invention is not intended to be limited to the following.

Figure 2:
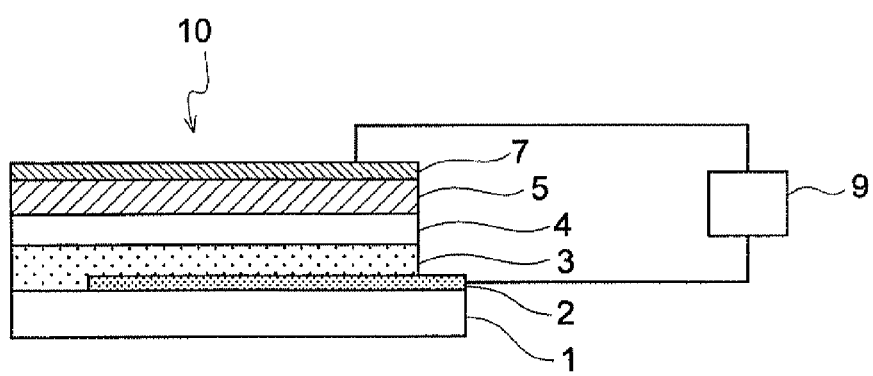
FIG. 2 is a schematic configuration diagram showing a display device according to another exemplary embodiment of the invention.
Figure 3:
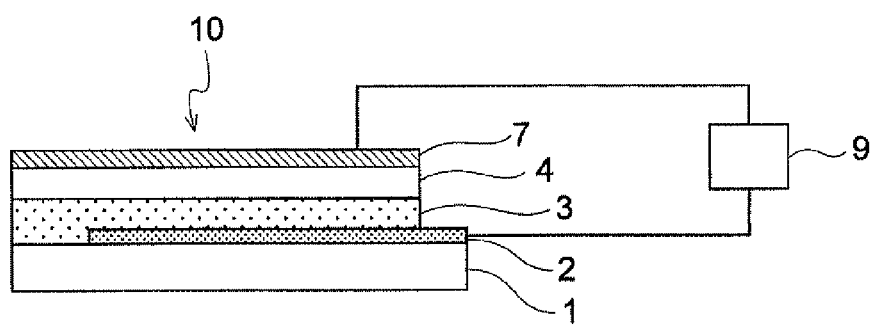
FIG. 3 is a schematic configuration diagram showing a display device according to another exemplary embodiment of the invention.
Figure 4:
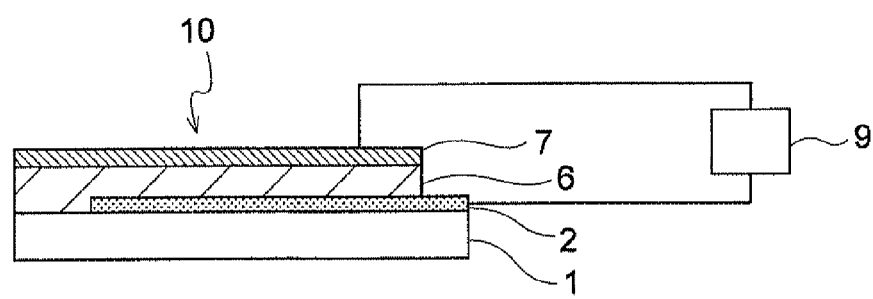
FIG. 4 is a schematic configuration diagram showing a display device according to another exemplary embodiment of the invention.

FIGS. 1 to 4 are schematic cross-sectional views for explaining the layer configurations of the organic electroluminescent device of the exemplary embodiment, and the instances shown in FIGS. 1, 2 and 3 are examples in which the organic compound layer consists of plural layers, while the instance shown in FIG. 4 represent an example in which the organic compound layer consists of a single layer. In addition, FIGS. 1 to 4 will be explained by assigning a same reference numeral to those parts having a same function.

The organic electroluminescent device 10 shown in FIG. 1 is formed by sequentially layering, on a transparent insulator substrate 1, a transparent electrode 2, a light emitting layer 4, an electron transport layer 5, and a back electrode 7, thus corresponding to the layer configuration (1).

Here, the electron transport layer 5 may consist of an electron injection layer, or may consist of an electron transport layer and an electron injection layer. In that situation, layering is achieved in the order of the electron transport layer, the electron injection layer and the back electrode 7, from the side of the light emitting layer 4 toward the side of the back electrode 7.

The light emitting layer 4 may be a light emitting layer having charge transport capability 6. That is, the configuration may include a transparent electrode 2, a light emitting layer having charge transport capability 6, an electron transport layer 5, and a back electrode 7 sequentially layered on a transparent insulator substrate 1.

The organic electroluminescent device 10 shown in FIG. 2 is formed by sequentially layering, on a transparent insulator substrate 1, a transparent electrode 2, a hole transport layer 3, a light emitting layer 4, an electron transport layer 5, and a back electrode 7, thus corresponding to the layer configuration (2).

Here, the hole transport layer 3 may consist of a hole injection layer, or may consist of a hole transport layer and a hole injection layer. In that situation, layering is achieved in the order of the hole injection layer, the hole transport layer and the light emitting layer 4, from the side of the transparent electrode 2 toward the side of the back electrode 7.

The electron transport layer 5 may consist of an electron injection layer, or may consist of an electron transport layer and an electron injection layer. In that situation, layering is achieved in the order of the electron transport layer, the electron injection layer and the back electrode 7, from the side of the light emitting layer 4 toward the side of the back electrode 7.

The light emitting layer 4 may be a light emitting layer having charge transport capability 6. That is, the configuration may include a transparent electrode 2, a hole transport layer 3, a light emitting layer having charge transport capability 6, an electron transport layer 5, and a back electrode 7 sequentially layered on a transparent insulator substrate 1.

The organic electroluminescent device 10 shown in FIG. 3 is formed by sequentially layering, on a transparent insulator substrate 1, a transparent electrode 2, a hole transport layer 3, a light emitting layer 4, and a back electrode 7, thus corresponding to the layer configuration (3).

Here, the hole transport layer 3 may consist of a hole injection layer, or may consist of a hole transport layer and a hole injection layer. In that situation, layering is achieved in the order of the hole injection layer, the hole transport layer and the light emitting layer 4, from the side of the transparent electrode 2 toward the side of the back electrode 7.

The light emitting layer 4 may be a light emitting layer having charge transport capability 6. That is, the configuration may include a transparent electrode 2, a hole transport layer 3, a light emitting layer having charge transport capability 6, and a back electrode 7 sequentially layered on a transparent insulator substrate 1.

The organic electroluminescent device 10 shown in FIG. 4 is formed by sequentially layering, on a transparent insulator substrate 1, a transparent electrode 2, a light emitting layer having charge transport capability 6, and a back electrode 7.

In the case of using a top emission structure or using transparent electrodes for both the positive electrode and the negative electrode so as to construct a transmission type, plural layer configurations of FIGS. 1 to 4 may be stacked.

To a layer containing the thiazolothiazole compound represented by formula (I), any of the functions such as light emitting capability, hole transport capability and electron transport capability may be imparted, based on the function of the layer containing the compound.

For example, in the case of the layer configuration of the organic electroluminescent device 10 shown in FIG. 1, the thiazolothiazole compound represented by formula (I) may be contained in any of the light emitting layer 4 and the electron transport layer 5, and exerts its action as any of the light emitting layer 4 and the electron transport layer 5.

In the case of the layer configuration of the organic electroluminescent device 10 shown in FIG. 2, the thiazolothiazole compound represented by formula (I) may be contained in any of the hole transport layer 3, the light emitting layer 4 and the electron transport layer 5, and exerts its action as any of the hole transport layer 3, the light emitting layer 4 and the electron transport layer 5.

In the case of the layer configuration of the organic electroluminescent device 10 shown in FIG. 3, the thiazolothiazole compound represented by formula (I) may be contained in any of the hole transport layer 3 and the light emitting layer 4, and exerts its action as any of the hole transport layer 3 and the light emitting layer 4.

In the case of the layer configuration of the organic electroluminescent device 10 shown in FIG. 4, the thiazolothiazole compound represented by formula (I) may be contained in the light emitting layer 6, and exerts its action as the light emitting layer having charge transport capability 6.

Hereinafter, each of the layers will be explained in detail. The reference numerals will be omitted in the following.

In the layer configurations of the organic electroluminescent device shown in FIGS. 1 to 4, the transparent insulator substrate may be transparent or semi-transparent in order to extract the emitted light, and may be formed from, for example, glass, quartz, metal foil, a resin film or the like, but is not intended to be limited to these materials. Examples of the resin constituting the resin film include a methacrylic resin (for example, polymethyl methacrylate (PMMA) or the like), a polyester resin (for example, a polyethylene terephthalate (PET), polyethylene naphthalate (PEN), or the like), and a polycarbonate resin. A moisture permeation preventing layer that suppresses water permeability or gas permeability may be provided on the front surface or the back surface of the transparent insulator substrate. As the material of the moisture permeation preventing layer (gas barrier layer), inorganic substances such as silicon nitride and silicone oxide may be used. The moisture permeation preventing layer is formed by, for example, a sputtering method or the like.

Here, the term "transparent or semi-transparent" means that the transmissivity of light in the visible region is 10% or greater, and more specifically the transmissivity may be 75% or greater.

The transparent electrode may be transparent or semi-transparent in order to extract the emitted light, similarly to the case of the transparent insulator substrate, and may have a large work function so as to carry out the injection of holes. Examples thereof include those having a work function of 4 eV or greater.

Specific examples of the transparent electrode include oxide films made of indium tin oxide (ITO), tin oxide (NESA), indium oxide, zinc oxide, zinc indium oxide or the like; or deposited or sputtered gold, platinum palladium, and the like.

The sheet resistance of the transparent electrode 2 may be a lower value, and the value may be specifically several hundred Ω/□ or lower, and more specifically 100Ω/□ or lower.

The transmissivity of light in the visible region in the transparent electrode may be specifically 10% or higher, and more specifically the transmissivity may be 75% or higher.

In the case of the layer configurations of the organic electroluminescent devices shown in FIGS. 1 to 3, the electron transport layer, the hole transport layer or the like may be formed of only the thiazolothiazole compound represented by formula (I), to which function (electron transport capability or hole transport capability) has been imparted depending on the purpose. However, for the purpose of controlling the hole mobility, the layer may be formed by mixing and dispersing a hole transporting material other than the thiazolothiazole compound represented by formula (I), into the thiazolothiazole compound represented by formula (I), in an amount in the range of from 0.1% by weight to 50% by weight with respect to the thiazolothiazole compound.

Examples of this hole transporting material include a tetraphenylenediamine compound, a triphenylamine compound, a carbazole compound, a stilbene compound, an arylhydrazone compound, and a porphyrin compound, and more specific examples include a tetraphenylenediamine compound or a triphenylamine compound.

Similarly, in the case of controlling the electron mobility, the layer may be formed by mixing and dispersing an electron transporting material other than the thiazolothiazole compound represented by formula (I), into the thiazolothiazole compound represented by formula (I), in an amount in the range of from 0.1% by weight to 50% by weight with respect to the thiazolothiazole compound.

Examples of this electron transporting material include an oxadiazole compound, a nitro-substituted fluorenone compound, a diphenoquinone compound, a thiopyrane dioxide compound, a silole compound, a chelate type organometallic complex, a polynuclear or fused aromatic ring compound, a perylene compound, a triazole compound, a fluorenylidenemethane compound, and the like.

When it is necessary to control both the hole mobility and the electron mobility, the layer may be formed by incorporating both of a hole transporting material and an electron transporting material into the thiazolothiazole compound represented by formula (I).

Furthermore, a resin (polymer) or an additive may be added to the thiazolothiazole compound represented by formula (I), to form the layer.

Specific examples of the resin include (electroconductive) resins such as a polycarbonate resin, a polyester resin, a methacrylic resin, an acrylic resin, a polyvinyl chloride resin, a cellulose resin, a urethane resin, an epoxy resin, a polystyrene resin, a polyvinyl acetate resin, a styrene-butadiene copolymer, a vinylidene chloride-acrylonitrile copolymer, a vinyl chloride-vinyl acetate-maleic anhydride copolymer, a silicone resin, a poly-N-vinylcarbazole resin, a polysilane resin, polythiophene and polypyrrole, and the like. Furthermore, examples of the additive include an antioxidant, an ultraviolet absorbent, a plasticizer and the like, that are known in the art.

In the case of providing at least one of the hole injection layer or the electron injection layer, a hole injecting material or an electron injecting material may be added to the layer.

Examples of the hole injecting material include a phenylenediamine compound, a phthalocyanine compound, an indanthrene compound, a polyalkylenedioxythiophene compound, and the like. These materials may also be added with a Lewis acid, sulfonic acid or the like.

Examples of the electron injecting material include a metal (for example, Li, Ca, Sr, or the like), a metal fluoride (for example, LiF, $MgF_2$, or the like), a metal oxide (for example, MgO, $Al_2O_3$, LiO or the like), and the like.

In the case of the layer configurations of the organic electroluminescent devices shown in FIGS. 1 to 4, the light emitting layer contains a light emitting material. In particular, the light emitting layer may contain the thiazolothiazole compound represented by formula (I) together with a light emitting material, and in the case of a light emitting layer having charge transport capability, the thiazolothiazole compound represented by formula (I) is used in combination with a light emitting material.

As for the light emitting material, for example, a compound in the solid state is used. The light emitting material may be a low molecular weight compound or a macromolecular compound. Specific examples of the light emitting material being a low molecular weight compound include a chelate type organometallic complex, a polynuclear or fused aromatic ring compound, a perylene compound, a coumarin compound, a styrylarylene compound, a silole compound, an oxazole compound, an oxathiazole compound, an oxadiazole compound, and the like. Specific examples of the light emitting material being a macromolecular compound include a polyparaphenylene compound, a polyparaphenylenevinylene compound, a polythiophene compound, a polyacetylene compound, and the like.

More specific examples of the light emitting material include the light emitting materials (VII-1) to (VII-17) shown below, but are not intended to be limited to these. Furthermore, in the light emitting material (VII-17), Z may be a group selected from the following (VII-18) to (VII-28). n, h and g each represent an integer of 1 or greater.
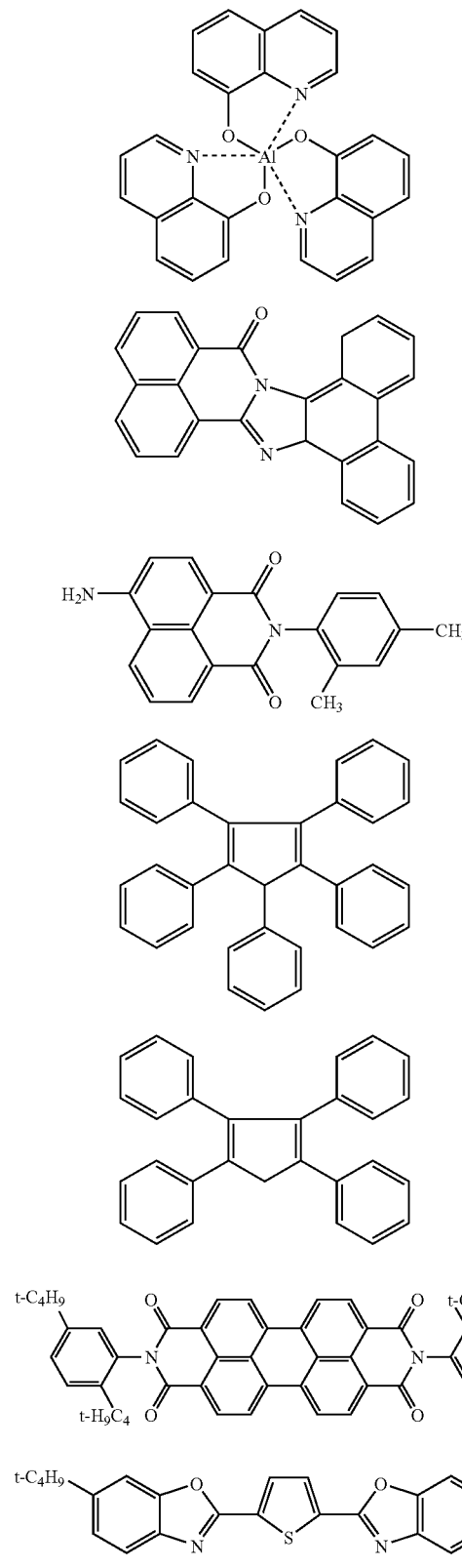
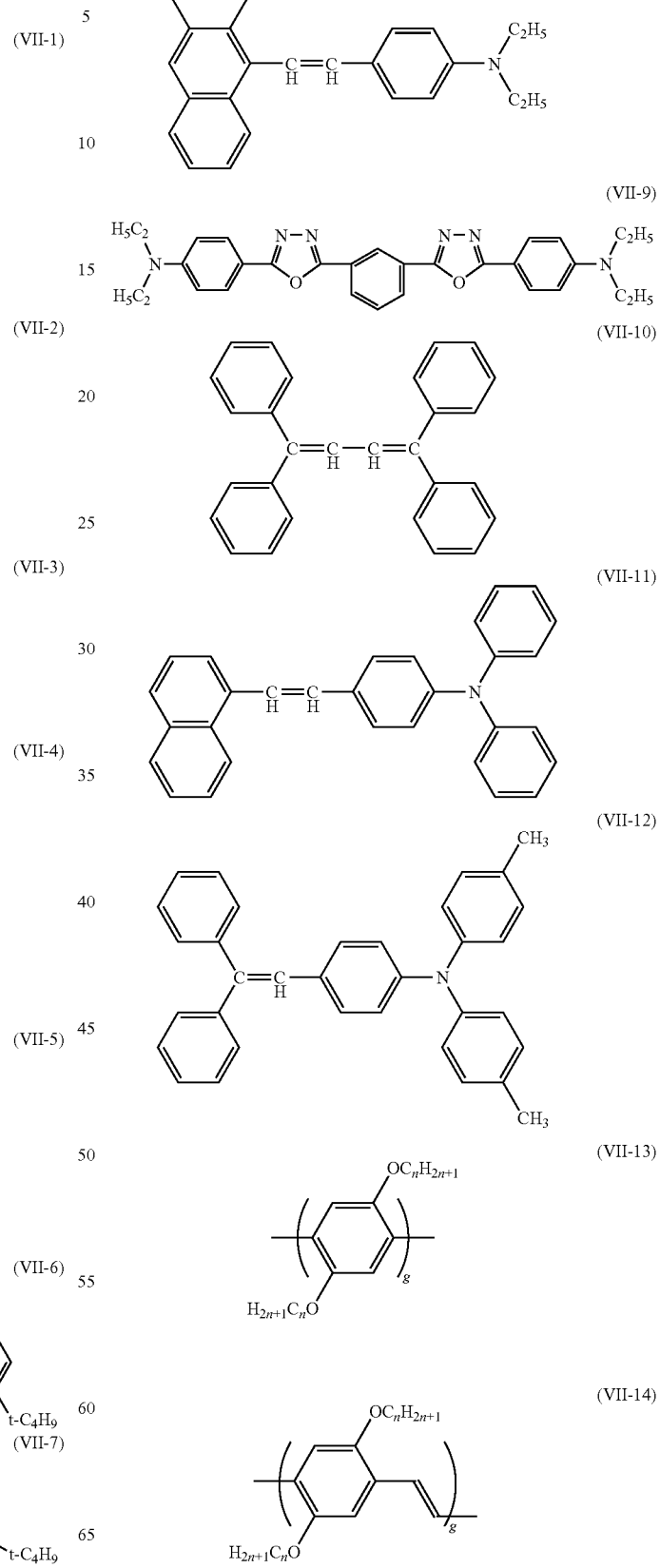

(VII-15)

(VII-16)

(VII-17)

(VII-18) —(CH$_2$)$_g$—

(VII-19) —C(CH$_3$)$_2$—

(VII-20) —O—

(VII-21) —S—

(VII-22)

(VII-23)

(VII-24) —C(CF$_3$)$_2$—

(VII-25) —Si(CH$_3$)$_2$—

(VII-26)

(VII-27)

(VII-28)

In the light emitting layer, the light emitting material may be doped with a colorant compound that is different from the light emitting material, as a guest material. The doping ratio of the colorant compound may be specifically from about 0.001% by weight to 40% by weight, and more specifically from about 0.001% by weight to 10% by weight.

Specific examples of this colorant compound include a coumarin compound, a DCM compound, a quinacridone compound, a perimidone compound, a benzopyrane compound, a rhodamine compound, a benzothioxanthene compound, a rubrene compound, a porphyrin compound, a complex containing a transition metal atom or a lanthanide atom (for example, a complex compound of ruthenium, rhodium, palladium, silver, rhenium, osmium, iridium, platinum, neodymium, europium, gold or the like), and the like. In particular, specific examples of the light emitting compound include an iridium metal complex, a europium complex, a platinum complex, and the like. More specific examples include the following light emitting compounds (VIII-1) to (VIII-6), but are not intended to be limited to these.

(VIII-1)

(VIII-2)

(VIII-3)

(VIII-4)

(VIII-5)

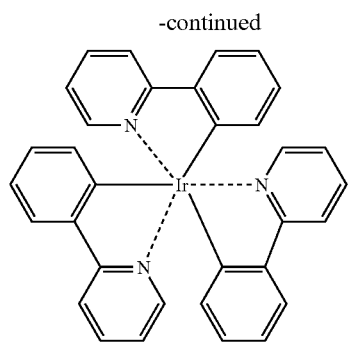

(VIII-6)

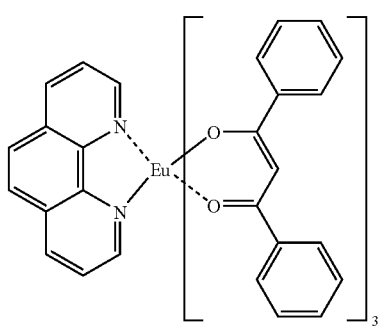

In the case of the layer configurations of the organic electroluminescent devices shown in FIGS. 1 to 4, the back electrode may be formed of, for example, a metal, a metal oxide, a metal fluoride, or the like.

Examples of the metal include magnesium, aluminum, gold, silver, indium, lithium, and calcium, or alloys thereof. Examples of the metal oxide include lithium oxide, magnesium oxide, aluminum oxide, indium tin oxide, tin oxide, indium oxide, zinc oxide, zinc indium oxide, and the like. Examples of the metal fluoride include lithium fluoride, magnesium fluoride, strontium fluoride, calcium fluoride, and aluminum fluoride.

The back electrode may be provided with a protective layer (not shown in the diagram) thereon. Specific examples of the material of the protective layer include a metal (for example, In, Sn, Pb, Au, Cu, Ag, Al, or the like), a metal oxide (for example, MgO, $SiO_2$, $TiO_2$, or the like), and a resin (for example, a polyethylene resin, a polyurea resin, a polyimide resin, or the like). In the formation of the protective layer, for example, a vacuum deposition method, a sputtering method, a plasma polymerization method, a CVD method, or a coating method is applied.

These organic electroluminescent devices shown in FIGS. 1 to 4 may be produced by forming individual layers sequentially on a transparent electrode in accordance with each of the layer configurations of the organic electroluminescent devices. Here, the hole transport layer, the light emitting layer, the electron transport layer, and the light emitting layer having charge transport capability, as well as the hole injection layer and the electron injection layer may be formed by depositing the respective materials by a vacuum deposition method, or by dissolving or dispersing the respective materials in an appropriate organic solvent, and coating the transparent electrode with the obtained coating liquid by a spin coating method, a casting method, a dipping method, an inkjet method or the like.

Among these, the inkjet method may be used which may include, as the method for producing an organic electroluminescent device, a coating step of applying, by an inkjet method, a coating solution prepared by dissolving the constituent components of the organic compound layer in a solvent.

In the case of using an inkjet method, when a coating liquid for organic compound layer is used instead of ink, and the coating liquid for organic compound layer is ejected in the form of liquid droplets, from a nozzle of a liquid droplet ejecting head, an organic compound layer having a desired thickness and a desired shape is formed at a desired position on the substrate.

In regard to the liquid droplet ejecting head, use is made of a head used in inkjet printers, in terms of the fundamental configuration or principle. That is, a method of ejecting a coating liquid for organic compound layer from a nozzle in the form of liquid droplets, by applying an external stimulus such as pressure or heat to the coating liquid for organic compound layer (that is, a piezo inkjet system using a piezoelectric device, a thermal inkjet system utilizing the thermal boiling phenomenon, or the like), is utilized.

In the production of the organic electroluminescent device according to the exemplary embodiment, the external stimulus may be pressure, rather than heat.

An apparatus that is used in the production of the organic electroluminescent device according to the exemplary embodiment using an inkjet method, may include, in addition to the liquid droplet ejecting head mentioned above, for example, a fixing or conveying unit that fixes or conveys a substrate or the like, onto which an organic electroluminescent device is formed; a liquid droplet ejecting head scanning unit that scans with the liquid droplet ejecting head in the plane direction of the substrate; and the like, according to necessity.

The hole transport layer, the light emitting layer, the electron transport layer, and the light emitting layer having charge transport capability, and the hole injection layer and the electron injection layer may each have a thickness of 10 tin or less, and more specifically in the range of from 0.01 µm to 5 µm.

The respective materials mentioned above (the non-conjugate type polymer, light emitting material, and the like) may be dispersed in a molecular dispersed state, or in a particulate state of microcrystals or the like.

In the case of the organic electroluminescent devices shown in FIGS. 1 and 2, the organic electroluminescent device according to the exemplary embodiment may be obtained by forming the back electrode on the electron transport layer or the electron injection layer, by a vacuum deposit method, a sputtering method or the like.

In the case of the organic electroluminescent devices shown in FIGS. 3 and 4, the organic electroluminescent device according to the exemplary embodiment may be obtained by forming the back electrode on the light emitting layer (including the light emitting layer having charge transport capability), by a vacuum deposit method, a sputtering method or the like.

The organic electroluminescent device according to the exemplary embodiment may be used in the fields of, for example, display devices, electronic paper, backlight, illuminating light sources, exposure apparatuses for electrophotography, signs, signboards, and the like.

The coating liquid for organic compound layer that is used in the inkjet method is not particularly limited in terms of the composition or properties, but the viscosity of the coating liquid for organic compound layer may be specifically in the range of from 0.01 cps to 1000 cps, and more specifically in the range of from 1 cps to 100 cps at 25° C.

Next, the configuration of the display medium (device) according to the exemplary embodiment will be described in detail.

The display device of the exemplary embodiment includes the organic electroluminescent device of the exemplary embodiment, and a driving unit for driving the organic electroluminescent device.

A specific example of the display device may be provided with, as the driving unit, a voltage applying apparatus 9 that is connected to a pair of electrodes (electrode 2 and back electrode 7) of the organic electroluminescent device as shown in FIGS. 1 to 4, and is intended to apply a direct current voltage to the pair of electrodes.

As a method of driving an organic electroluminescent device using the voltage applying apparatus 9, for example, a direct current voltage of from 4 V to 20 V, with a current density of from 1 mA/cm$^2$ to 200 mA/cm$^2$, is applied to the pair of electrodes, and thereby the organic electroluminescent device is made to emit light.

The organic electroluminescent device of the exemplary embodiment has been explained in terms of the configuration of a minimal unit (single pixel unit), but the electroluminescent device is applied to, for example, a display device including the pixel units (organic electroluminescent devices) in at least one of a matrix arrangement or a segment arrangement. In the case where the organic electroluminescent devices are in a matrix arrangement, only the electrodes may be in a matrix arrangement, or both the electrodes and the organic compound layers may be in a matrix arrangement. On the other hand, in the case where the organic electroluminescent devices of the exemplary embodiment are in a segment arrangement, only the electrodes may be in a segment arrangement, or both the electrodes and the organic compound layers may be in a segment arrangement. Here, the organic compound layers in a matrix arrangement or a segment arrangement may be easily formed by, for example, employing the inkjet method described above.

In regard to the mode of driving the display device, conventionally known technologies are applied. For example, simple matrix driving in which plural row electrodes and column electrodes are arranged, and while scan driving of the row electrodes is carried out, the column electrodes are collectively driven in accordance with the image data corresponding to the respective row electrodes; active matrix driving based on the pixel electrodes disposed in the respective pixel; or the like is utilized.

EXAMPLES

Hereinafter, the exemplary embodiments of the invention will be specifically explained by way of Examples. However, these Examples are not intended to limit the exemplary embodiments.

Here, $^1$H-NMR spectroscopy ($^1$H-NMR, solvent: CDCl$_3$, trade name: UNITY-300, manufactured by Varian Inc., 300 MHz) and IR spectroscopy (KBr pellet method, Fourier-transformed infrared spectrophotometer (trade name: FT-730, manufactured by Horiba, Ltd.; resolution power 4 cm$^{-1}$)) were used for the identification of the intended products.

Synthesis Example 1

Synthesis of Exemplified Compound 1
<Synthesis of Compound III-a>

In a 200-ml three-necked flask, 5.3 g (45 mmol) of rubeanic acid and 20 g (180 mmol) of 2-thiophenaldehyde are dissolved in 100 ml of N,N-dimethylformamide (hereinafter, referred to as DMF). This solution is magnetically stirred for 5 hours at 150° C., and then is cooled to 25° C. This reaction liquid is added to a 2-L beaker containing 1 L of purified water, and the mixture is magnetically stirred for 30 minutes at 25° C. After stirring is completed, crystals precipitated therefrom are collected by filtration through suction filtration, and are washed with 1 L of purified water. The obtained crystals are further washed with 100 ml of methanol, and are vacuum dried for 15 hours at 60° C. After dried, the crystals are dissolved in 100 ml of tetrahydrofuran (hereinafter, referred to as THF), and the solution is subjected to silica gel short column chromatography, to obtain 6.4 g of the compound III-a. It is confirmed by $^1$H-NMR and IR that the compound is consistent with the intended product.

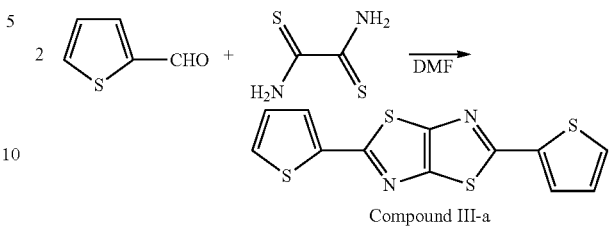

Compound III-a

<Synthesis of Compound IV-a>

In a nitrogen atmosphere, 4.5 g (15 mmol) of the compound III-a and 8.0 g (45 mmol) of NBS are added into a 500-ml three-necked flask, and the substances are dissolved in 200 ml of DMF. This solution is magnetically stirred for 7 hours at 60° C., and thus the reaction is completed. The reaction liquid is cooled to 25° C., and then is added to a 2-L beaker containing 1 L of purified water. The mixture is magnetically stirred for 30 minutes at 25° C. After stirring is completed, crystals precipitated therefrom are collected by filtration through suction filtration, and are washed with 1 L of purified water. The obtained crystals are vacuum dried for 15 hours at 60° C., and then are recrystallized twice from N-methylpyrrolidone (hereinafter, referred to as NMP), to obtain 3.3 g of the compound IV-a as yellow crystals. It is confirmed by $^1$H-NMR and IR that the compound is consistent with the intended product.

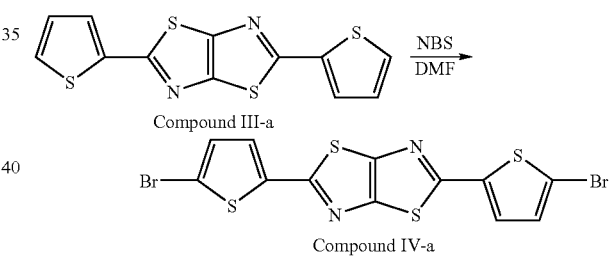

Compound III-a

Compound IV-a

<Synthesis of Exemplified Compound 1>

In a nitrogen atmosphere, 0.23 g (0.20 mmol) of tetrakistriphenylphosphine palladium(0) is dissolved in 100 ml of NMP in a 300-ml three-necked flask. To this solution, 1.84 g (4.0 mmol) of the compound IV-a, 8.0 ml of a 2 M aqueous solution of sodium carbonate, and 1.56 g (8.8 mmol) of 4-n-butylphenyl boronic acid are added in this order, and the mixture is magnetically stirred under reflux in an oil bath at 220° C. for 5 hours. After the completion of reaction is confirmed by $^1$H-NMR, the reaction liquid is cooled to 25° C., and is poured into a 2-L beaker containing 1 L of purified water. The mixture is magnetically stirred for 30 minutes at 25° C. After stirring is completed, crystals precipitated therefrom are collected by filtration through suction filtration, and are washed with 1 L of purified water. The obtained crystals are further washed with 100 ml of methanol and 100 ml of toluene, and are vacuum dried for 15 hours at 60° C. These crystals are added in 150 ml of NMP and are recrystallized. The crystals are further subjected to purification by sublimation, to obtain 1.0 g of the Exemplified Compound 1 as orange-colored crystals. It is confirmed by $^1$H-NMR and IR that the compound is consistent with the intended product.

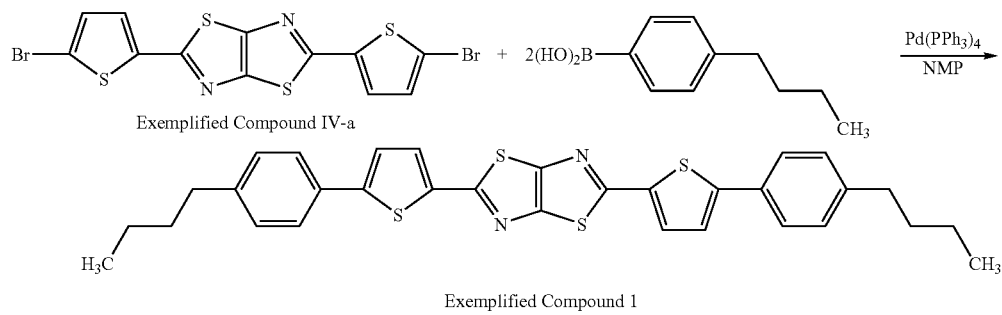

Exemplified Compound IV-a

Exemplified Compound 1

Synthesis Example 2

Synthesis of Exemplified Compound 4
<Synthesis of Compound V-a>

In a nitrogen atmosphere, 10 ml (16 mmol) of a 1.6 M n-butyllithium/hexane solution is added to a 100-ml three-necked flask cooled to −80° C. This solution is cooled to −80° C., and then 10 ml of THF maintained at −60° C. is added dropwise thereto from a dropping funnel. Subsequently, 3.1 g (16 mmol) of 1-bromo-4-n-octylbenzene maintained at −60° C. is added dropwise to the mixture from a dropping funnel. This mixture is stirred for one hour at −40° C., and then a solution of 2.3 g (22 mmol) of trimethyl borate in THF (10 ml) maintained at −40° C. is added thereto from a dropping funnel. Thereafter, the mixture is slowly heated to 10° C. over 2 hours, and then 50 ml of a 10% aqueous solution of HCl at 0° C. is added thereto. The mixture is extracted with 100 ml of toluene. This extract is washed three times with 100 ml of purified water, and then is dried with sodium sulfate. Toluene is distilled off under reduced pressure, and 3.3 g of a residue is obtained. This residue is further washed with a mixed liquid of 100 ml of purified water and 100 ml of hexane, and thus 2.0 g of the compound V-a, which is 4-n-octylphenylboronic acid, is obtained. It is confirmed by $^1$H-NMR and IR that the compound is consistent with the intended product.

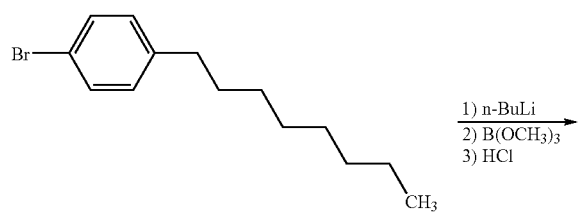

1) n-BuLi
2) B(OCH$_3$)$_3$
3) HCl

-continued

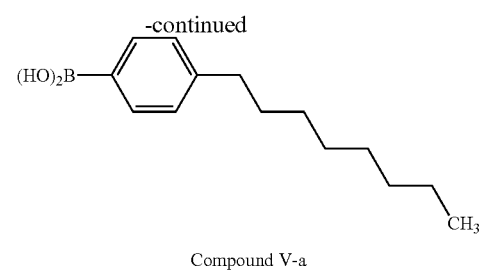

Compound V-a

<Synthesis of Exemplified Compound 4>

In a nitrogen atmosphere, 0.11 g (0.10 mmol) of tetrakistriphenylphosphine palladium(0) is dissolved in 100 ml of NMP in a 300-ml three-necked flask. To this solution, 1.4 g (3.0 mmol) of the compound IV-a, 9.0 ml of a 2 M aqueous solution of sodium carbonate, and 1.4 g (6.0 mmol) of 4-n-octylphenyl boronic acid (compound V-a) are added in this order, and the mixture is magnetically stirred under reflux in an oil bath at 200° C. for 5 hours. After the completion of reaction is confirmed by $^1$H-NMR, the reaction liquid is cooled to 25° C., and is poured into a 2-L beaker containing 1 L of purified water. The mixture is magnetically stirred for 20 minutes at 25° C. After stirring is completed, crystals precipitated therefrom are collected by filtration through suction filtration, and are washed with 300 ml of purified water. The obtained crystals are further washed with 200 ml of methanol and 100 ml of toluene, and are vacuum dried for 15 hours at 60° C. These crystals are recrystallized using 200 ml of NMP, and subsequently the crystals are further subjected to purification by sublimation, to obtain 0.60 g of the Exemplified Compound 4 as orange-colored crystals. It is confirmed by $^1$H-NMR and IR that the compound is consistent with the intended product.

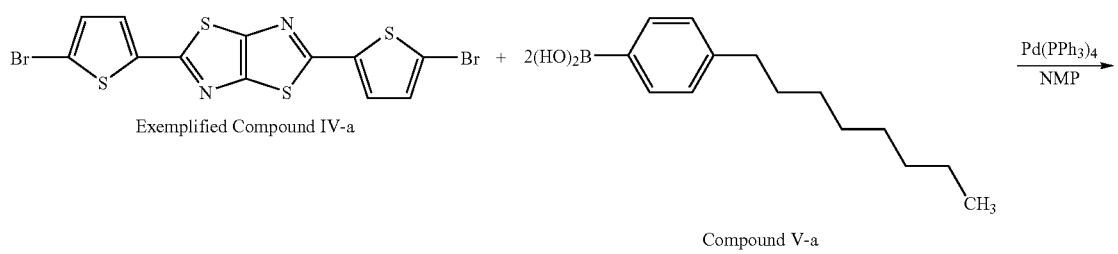

Exemplified Compound IV-a

Compound V-a

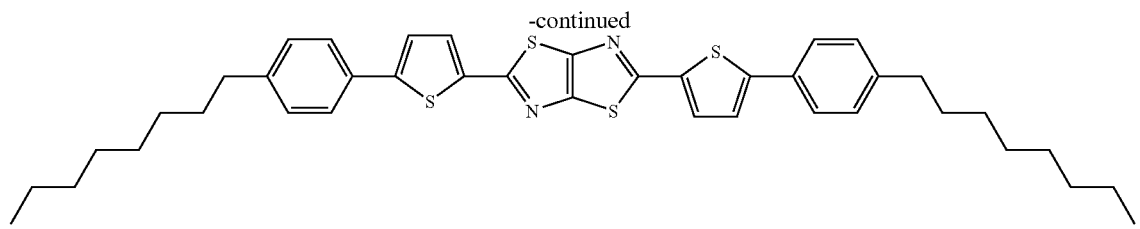

Exemplified Compound 4

Synthesis Example 3

Synthesis of Exemplified Compound 7
<Synthesis of Compound III-b>

18 g (150 mmol) of rubeanic acid, and 75 g (600 mmol) of 3-methylthiophene-2-aldehyde are added to a 1-L three-necked flask, and the mixture is dissolved in 350 ml of DMF. This solution is magnetically stirred for 5 hours in an oil bath at 150° C., and then is cooled to 25° C. This reaction liquid is added to a 2-L beaker containing 1 L of purified water, and is magnetically stirred for 30 minutes at 25° C. After stirring is completed, crystals precipitated therefrom are collected by filtration through suction filtration, and are washed with 1 L of purified water. The adhering black crystals are washed by adding 100 ml of toluene and 200 ml of methanol thereto and stirred ultrasonically and magnetically for 10 minutes. The washed crystals are collected by filtration through suction filtration, and thus 34 g of crude crystals are obtained. The crude crystals are further washed with 200 ml of methanol, and are vacuum dried for 15 hours at 60° C. After dried, the crystals are dissolved in 500 ml of monochlorobenzene, and are subjected to silica gel short column chromatography, to obtain 19 g of the compound III-b. It is confirmed by $^1$H-NMR and IR that the compound is consistent with the intended product.

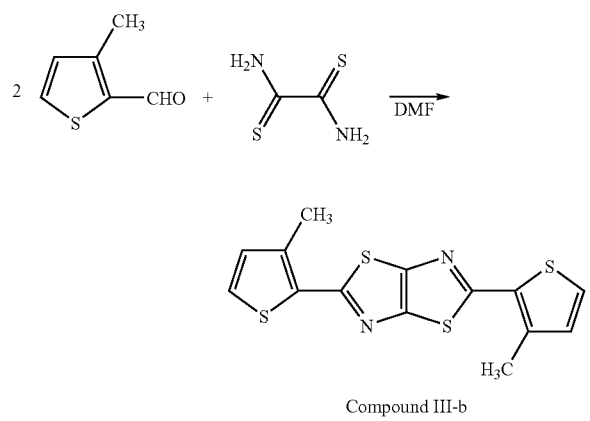

Compound III-b

<Synthesis of Compound IV-b>

In a nitrogen atmosphere, 19 g (57 mmol) of the compound III-b, and 23 g (129 mmol) of NBS are added to a 1-L three-necked flask, and the mixture is dissolved in 500 ml of DMF. This solution is magnetically stirred for 4 hours at 60° C., and thus the reaction is completed. The reaction liquid is cooled to 25° C., and then is added to a 2-L beaker containing 1 L of purified water. The mixture is magnetically stirred for 30 minutes at 10° C. After stirring is completed, crystals precipitated therefrom are collected by filtration through suction filtration, and are washed with 1 L of purified water and 200 ml of methanol. The crystals are vacuum dried for 15 hours at 60° C., and then are recrystallized twice with 300 ml of NMP. Thus, 21 g of the compound IV-b is obtained as yellow crystals. It is confirmed by $^1$H-NMR and IR that the compound is consistent with the intended product.

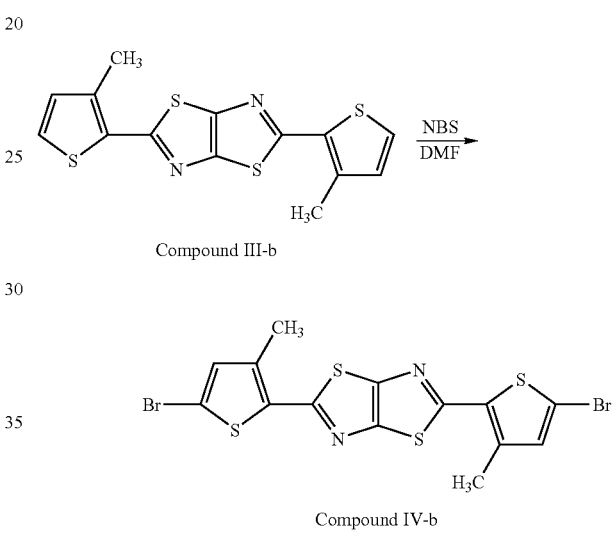

Compound IV-b

<Synthesis of Exemplified Compound 7>

In a nitrogen atmosphere, 0.16 g (0.14 mmol) of tetrakis-triphenylphosphine palladium(0) is dissolved in 100 ml of NMP in a 300-ml three-necked flask. To this solution, 2.2 g (4.5 mmol) of the compound IV-b, 9.0 ml of a 2 M aqueous solution of sodium carbonate, and 1.78 g (10 mmol) of 4-n-butylphenyl boronic acid are added in this order, and the mixture is magnetically stirred under reflux in an oil bath at 220° C. for 6 hours. After the completion of reaction is confirmed by $^1$H-NMR, this reaction liquid is cooled to 25° C., and is added to a 1-L beaker containing 500 ml of purified water. The mixture is magnetically stirred for 30 minutes at 25° C. After stirring is completed, crystals precipitated therefrom are collected by filtration through suction filtration, and are washed with 300 ml of purified water. The obtained crystals are further washed with 200 ml of methanol and 100 ml of hexane, and are vacuum dried for 15 hours at 60° C. These crystals are dissolved under heating in 200 ml of THF and 100 ml of toluene, and the solution is subjected to silica gel short column chromatography. Subsequently, recrystallization is performed using 300 ml of toluene, and thus 0.70 g of the Exemplified Compound 7 is obtained as orange-colored crystals. It is confirmed by $^1$H-NMR and IR that the compound is consistent with the intended product.

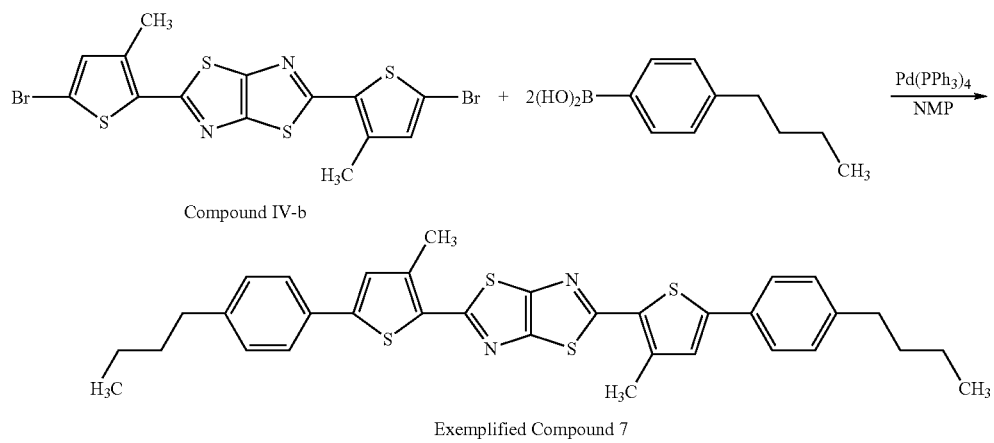

Compound IV-b

Exemplified Compound 7

Synthesis Example 4

Synthesis of Exemplified Compound 8

In a nitrogen atmosphere, 0.090 g (0.080 mmol) of tetrakistriphenylphosphine palladium(0) is dissolved in 50 ml of THF in a 200-ml three-necked flask. To this solution, 1.23 g (2.5 mmol) of the compound IV-b, 6.0 ml of a 2 M aqueous solution of sodium carbonate, and 1.24 g (5.3 mmol) of the compound V-a are added in this order, and the mixture is magnetically stirred under reflux for 12 hours. After the completion of reaction is confirmed by $^1$H-NMR, this reaction liquid is cooled to 25° C., and is added to a 1-L beaker containing 100 ml of a 5% aqueous solution of hydrochloric acid and 200 ml of toluene. The mixture is magnetically stirred for 30 minutes at 25° C. The toluene layer is separated, washed three times with 200 ml of purified water, and then dried with anhydrous sodium sulfate. The liquid is filtered, and then the solvent is distilled off under reduced pressure, to obtain 1.7 g of orange-colored solids. The solids are purified by silica gel column chromatography from a mixed solvent of toluene and THF (mixing weight ratio 1:2). Subsequently, recrystallization is carried out from toluene, and the product is vacuum dried for 15 hours. Thus, 1.2 g (yield: 70%) of the Exemplified Compound 8 is obtained as orange-colored crystals. It is confirmed by $^1$H-NMR and IR that the compound is consistent with the intended product.

Synthesis Example 5

Synthesis of Exemplified Compound 11

In a nitrogen atmosphere, 0.14 g (0.12 mmol) of tetrakistriphenylphosphine palladium(0) is dissolved in 100 ml of NMP in a 300-ml three-necked flask. To this solution, 1.85 g (4.0 mmol) of the compound IV-a, 8.0 ml of a 2 M aqueous solution of sodium carbonate, and 1.71 g (8.8 mmol) of 4-n-butoxyphenyl boronic acid are added in this order, and the mixture is magnetically stirred under reflux in an oil bath at 220° C. for 4 hours. After the completion of reaction is confirmed by $^1$H-NMR, the reaction liquid is cooled to 25° C., and is poured into a 2-L beaker containing 1 L of purified water. The mixture is magnetically stirred for 20 minutes at 25° C. After stirring is completed, crystals precipitated therefrom are collected by filtration through suction filtration, and are washed with 1 L of purified water. The obtained crystals are further washed with 200 ml of methanol and 250 ml of toluene, and are vacuum dried for 15 hours at 60° C. 150 ml of NMP is added to these crystals, and recrystallization is carried out. The crystals are further subjected to purification by sublimation, to obtain 1.0 g of the Exemplified Compound II as orange-colored crystals. It is confirmed by $^1$H-NMR and IR that the compound is consistent with the intended product.

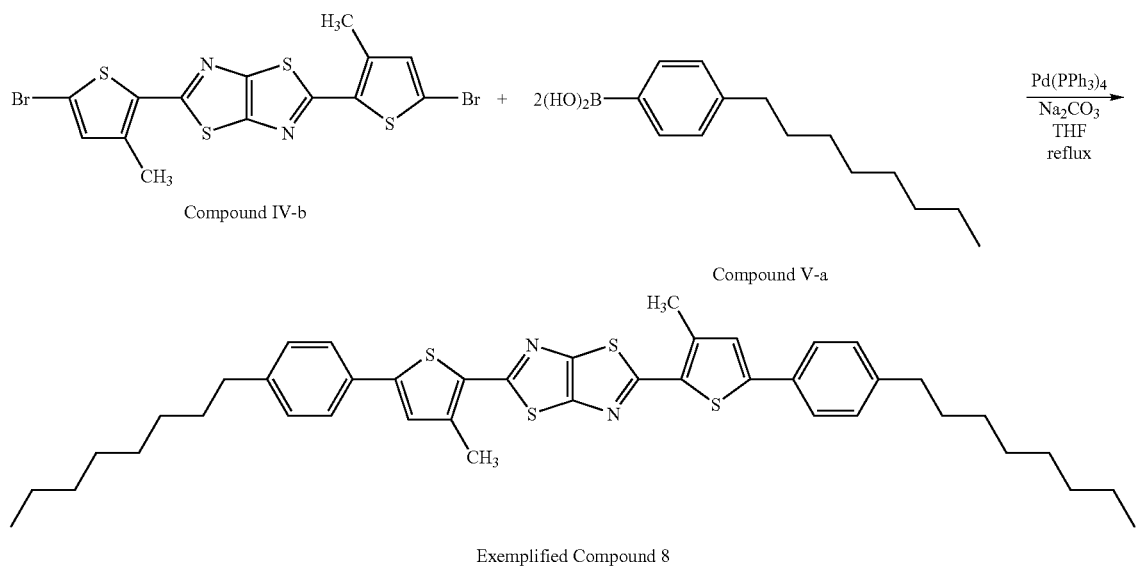

Compound IV-b

Compound V-a

Exemplified Compound 8

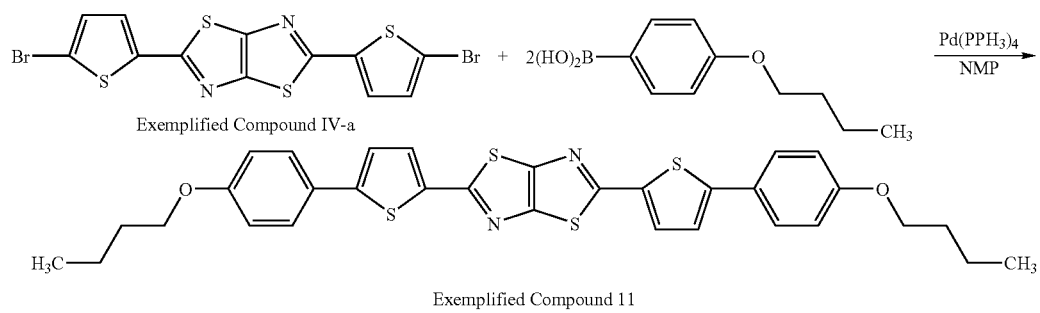

Exemplified Compound IV-a

Exemplified Compound 11

Synthesis Example 6

Synthesis of Exemplified Compound 25
Synthesis of Compound VI-a>
In a 500-ml four-necked flask, 60 g (305 mmol) of 3-n-octylthiophene is dissolved in 100 ml of DMF. This solution is cooled to 5° C., and a solution prepared by preliminarily dissolving 55 g (310 mmol) of N-bromosuccinimide (hereinafter, referred to as NBS) in 50 ml of DMF is added dropwise thereto from a constant pressure dropping funnel over 5 minutes. Subsequently, the mixture is magnetically stirred for one hour at 25° C., and then is added to a 1-L beaker containing 500 ml of purified water. The mixture is magnetically stirred for 20 minutes at 25° C. 300 ml of ethyl acetate is added to this solution, and the mixture is magnetically stirred for 10 minutes at 25° C. The ethyl acetate layer is separated and washed three times with 300 ml of purified water. The resultant is dried with anhydrous sodium sulfate and then filtered, and the solvent is distilled off under reduced pressure, to obtain 83 g of a yellow oily matter. This is subjected to vacuum distillation (1 to 3 mmHg, 120 to 130° C.), and thus 76 g (yield 93%) of a pale yellow oily matter (compound VI-a) is obtained.

reaction. After dropwise addition is completed, the mixture is stirred under reflux until magnesium disappears, and is cooled to 40° C. To this solution, 30 ml of DMF that has been preliminarily dried with calcium hydride, is added dropwise over 10 minutes. Then, the mixture is magnetically stirred for 30 minutes at 50° C. After the reaction is completed, the reaction liquid is cooled to 5° C., and is added into a 1-L beaker containing 400 ml of 10% hydrochloric acid and 300 ml of toluene. This mixture is magnetically stirred for 30 minutes at 25° C., and then the toluene layer is separated and washed three times with 300 ml of purified water. The resultant is dried with anhydrous sodium sulfate and filtered, and the solvent is distilled off under reduced pressure, to obtain 94 g of a red oily matter. This is subjected to vacuum distillation (1 to 3 mmHg, 140 to 150° C.), and thus 52 g (yield 64%) of a yellow oily matter (compound VI-b) is obtained. It is confirmed by $^1$H-NMR and IR that the compound is consistent with the intended product.

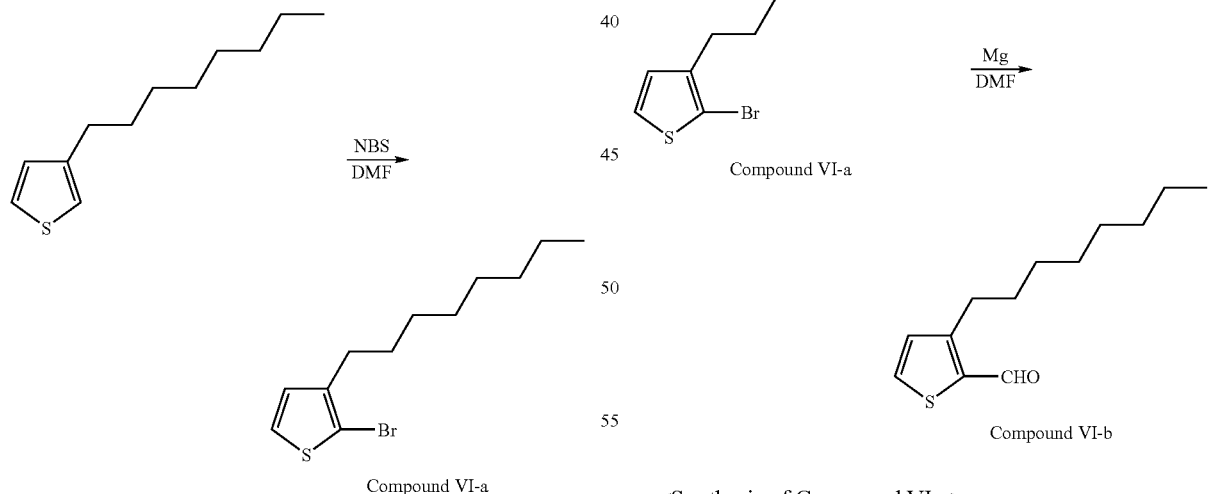

<Synthesis of Compound VI-b>
9.1 g (374 mmol) of magnesium and 100 ml of THF are added to a sufficiently dried 500-ml four-necked flask in a nitrogen atmosphere. To this mixture, 3 grains of iodine particles are added to activate the surface of the magnesium. Subsequently, the mixture is heated to 60° C., and a solution of 100 g (363 mmol) of the compound VI-a in 50 ml of THF is added dropwise thereto, along with the progress of the <Synthesis of Compound VI-c>
8.0 g (67 mmol) of rubeanic acid, and 60 g (267 mmol) of the compound VI-b are added to a 300-ml four-necked flask, and the mixture is dissolved in 60 ml of N,N-dimethylformamide. This solution is magnetically stirred for 4 hours at 150° C., and then is cooled to 25° C. This reaction liquid is added to a 1-L beaker containing 300 ml of purified water, and the mixture is magnetically stirred for 30 minutes at 25° C. 300 ml of toluene is further added thereto, and the mixture is magnetically stirred for 10 minutes. Then, the toluene layer is separated and washed three times with 300 ml of purified water. The resultant is dried with anhydrous sodium sulfate and filtered, and the solvent is distilled off under reduced pressure, to obtain a brown oily matter. 200 ml of methanol is added to this matter, and the raw materials are removed by decantation. 200 ml of hexane is added to the residue, and the mixture is cooled to 5° C. to crystallize the residue. This resultant is collected by filtration through suction filtration, and the residue obtained therefrom is washed by pouring 100 ml of methanol. Thus, 12 g (yield 38%) of orange-colored crystals (compound VI-c) are obtained. It is confirmed by ¹H-NMR and IR that the compound is consistent with the intended product.

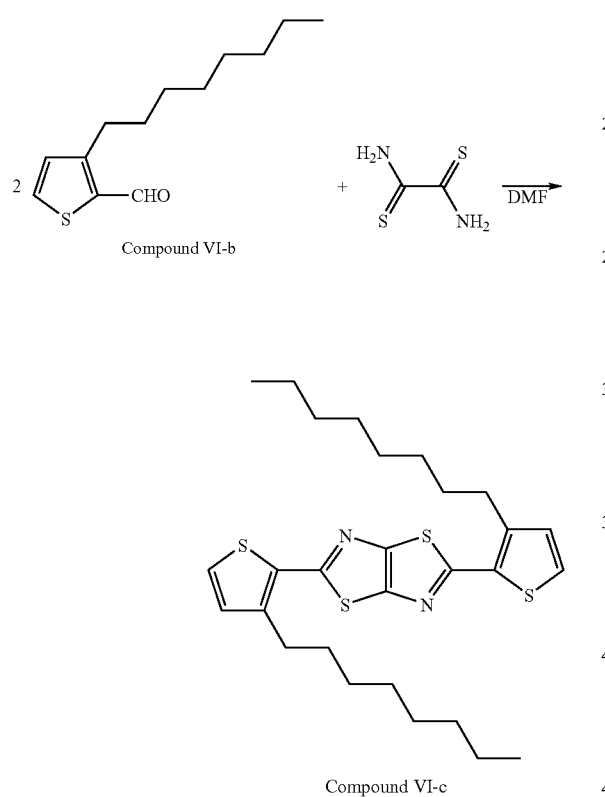

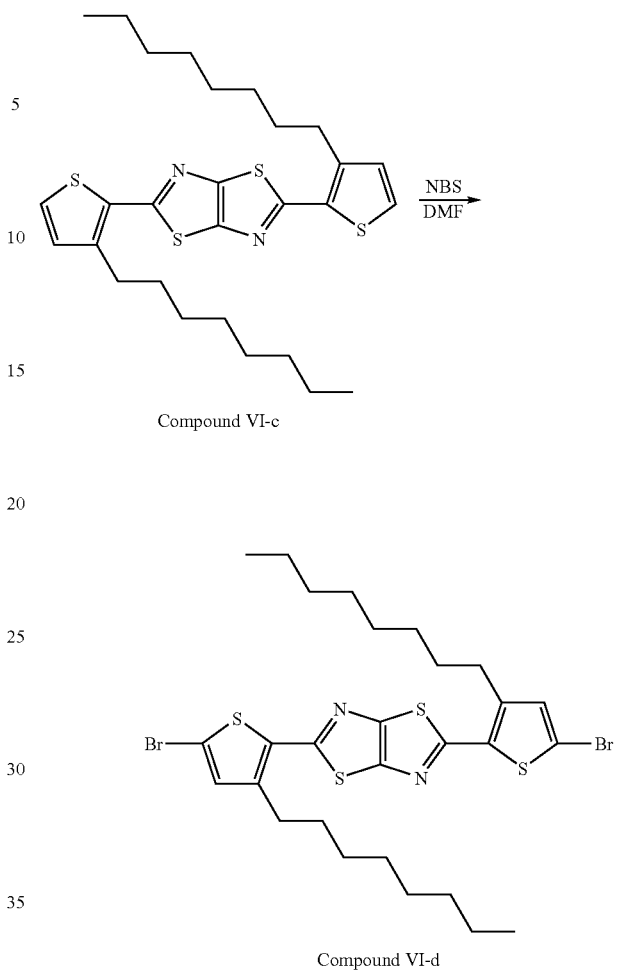

<Synthesis of Compound VI-d>

In a nitrogen atmosphere, 12 g (23 mmol) of the compound VI-c and 8.9 g (50 mmol) of NBS are added to a 500-ml three-necked flask, and the mixture is dissolved in 200 ml of DMF. This solution is magnetically stirred for one hour at 40° C., and thus the reaction is completed. This reaction liquid is cooled to 25° C., and then is added to a 2-L beaker containing 500 ml of purified water. The mixture is magnetically stirred for 30 minutes at 5° C. After stirring is completed, crystals precipitated therefrom are collected by filtration through suction filtration, and are washed with 1 L of purified water. Subsequently, the crystals are washed with 100 ml of methanol, and then are vacuum dried for 15 hours at 60° C. Thus, 12.2 g (yield 76%) of orange-colored crystals (compound VI-d) are obtained. It is confirmed by ¹H-NMR and IR that the compound is consistent with the intended product.

<Synthesis of Exemplified Compound 25>

In a nitrogen atmosphere, 0.10 g (0.090 mmol) of tetrakistriphenylphosphine palladium(0) is dissolved in 60 ml of THF in a 200-ml three-necked flask. To this solution, 2.06 g (3.0 mmol) of the compound VI-d, 7.0 ml of a 2 M aqueous solution of sodium carbonate, and 1.18 g (6.6 mmol) of 4-n-butylphenyl boronic acid are added in this order, and the mixture is magnetically stirred under reflux for 8 hours. After the completion of reaction is confirmed by ¹H-NMR, this reaction liquid is cooled to 25° C., and is added to a 1-L beaker containing 80 ml of a 5% aqueous solution of hydrochloric acid and 200 ml of toluene. The mixture is magnetically stirred for 30 minutes at 25° C. The toluene layer is separated, washed three times with 200 ml of purified water, and then dried with anhydrous sodium sulfate. The liquid is filtered, and then the solvent is distilled off under reduced pressure, to obtain 2.8 g of a red oily matter. Palladium is removed by silica gel filtration column chromatography, and then the resultant is washed with 50 ml of methanol and 20 ml of hexane. Subsequently, recrystallization is carried out using 100 ml of hexane. The resultant is vacuum dried for 15 hours. 1.8 g (yield: 78%) of the Exemplified Compound 25 is obtained as orange-colored crystals. It is confirmed by ¹H-NMR and IR that the compound is consistent with the intended product.

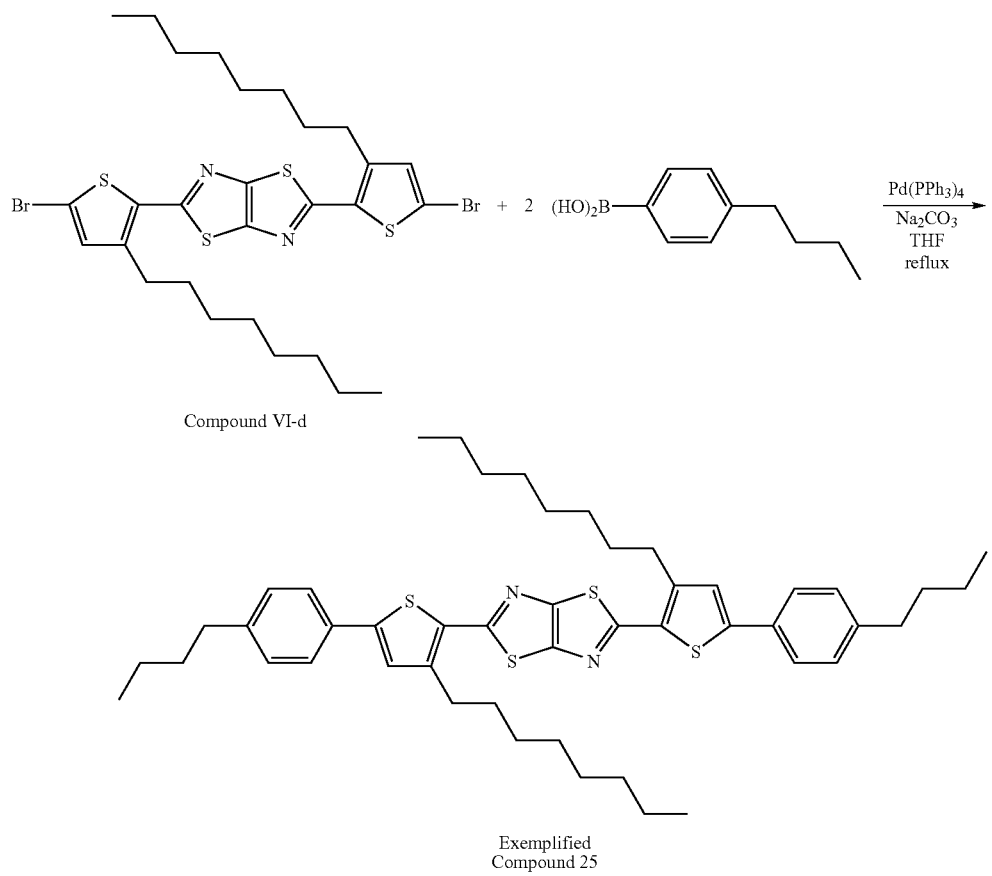

Example 1

ITO (manufactured by Sanyo Vacuum Industries Co., Ltd.) formed on a transparent insulating substrate (non-alkali glass substrate having a size of 25 mm×25 mm, and a thickness 0.7 mm) is patterned by photolithography using a strip-shaped photomask, and is subjected to etching. Thus, a strip-shaped ITO electrode (width 2 mm) is formed.

Subsequently, this ITO glass substrate is washed by ultrasonication with a neutral detergent, purified water, acetone (for electronic industries, manufactured by Kanto Chemical Co., Inc.) and isopropanol (for electronic industries, manufactured by Kanto Chemical Co., Inc.), for 5 minutes each, and then the substrate is dried on a spin coater.

Subsequently, the Exemplified Compound 25 as a hole transport material is vacuum deposited to form a thin film having a thickness of 0.050 μm, and thus a hole transport layer is formed.

Subsequently, on this hole transport layer, the light emitting material (VII-1) as a light emitting material is deposited to form a light emitting layer having a thickness of 0.055 μm.

Furthermore, on this light emitting layer, a metallic mask provided with strip-shaped slits is used, and a Mg—Ag alloy is deposited by co-deposition through the mask, to thereby form a back electrode having a width of 2 mm and a thickness of 0.15 μm so as to cross with the ITO electrode.

The effective area of the formed organic electroluminescent device is 0.04 cm$^2$.

Example 2

An organic electroluminescent device is produced in the same manner as in Example 1, except that the Exemplified Compound 4 is used instead of the Exemplified Compound 25.

Example 3

An organic electroluminescent device is produced in the same manner as in Example 1, except that the Exemplified Compound II is used instead of the Exemplified Compound 25.

Example 4

An organic electroluminescent device is produced in the same manner as in Example 1, except that the Exemplified Compound 7 is used instead of the Exemplified Compound 25.

Example 5

An organic electroluminescent device is produced in the same manner as in Example 1, except that the Exemplified Compound 8 is used instead of the Exemplified Compound 25.

Comparative Example 1

An organic electroluminescent device is produced in the same manner as in Example 1, except that the following compound (IX) is used instead of the Exemplified Compound 25.

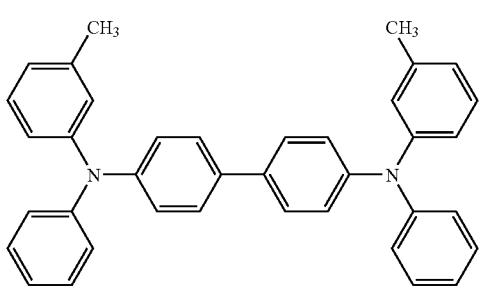

Comparative Example 2

An organic electroluminescent device is produced in the same manner as in Example 1, except that the following compound (X) is used instead of the Exemplified Compound 25.

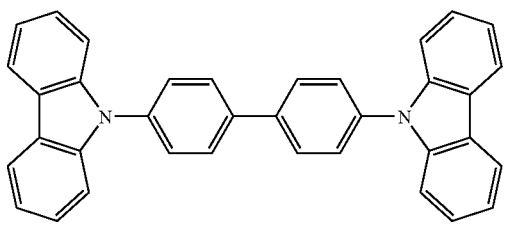

Comparative Example 3

An organic electroluminescent device is produced in the same manner as in Example 1, except that the following compound (XI) is used instead of the Exemplified Compound 25.

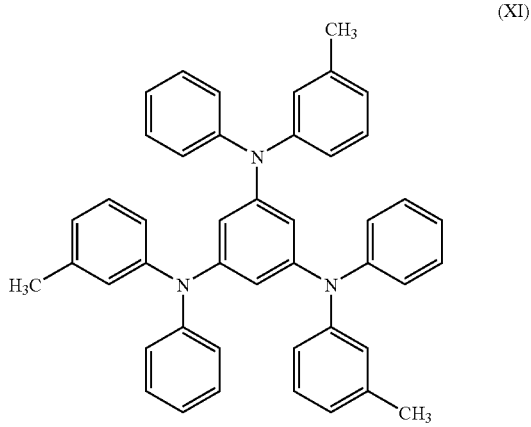

Comparative Example 4

An organic electroluminescent device is produced in the same manner as in Example 1, except that a thiazolothiazole compound represented by the following chemical formula (XII) is used instead of the Exemplified Compound 25.

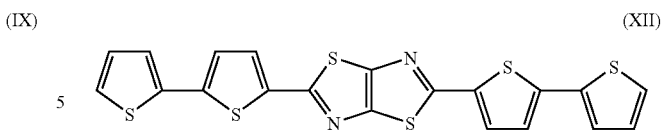

<Evaluation of Device Lifespan>

The organic electroluminescent device produced as described above is sealed with glass using an adhesive under dry nitrogen, and an evaluation is performed by using the ITO electrode as a positive electrode and the back electrode on the opposite side as a negative electrode.

The evaluation of the emission lifetime is carried out based on the relative time determined when the driving time at a time point where the luminance L of the device of Comparative Example 1 (initial luminance $L_0$: 400 cd/m$^2$) reaches a value satisfying the relationship: luminance L/initial luminance $L_0$=0.5, at room temperature (25° C.), is taken as 1.0, and based on the voltage increment (=driving voltage/initial driving voltage) at a time point where the luminance of the device reaches a value satisfying the relationship: luminance L/initial luminance $L_0$=0.5. The results are presented in Table 1.

TABLE 1

|  | Voltage increment (L/L$_0$ = 0.5) | Relative time (L/L$_0$ = 0.5) |
| --- | --- | --- |
| Example 1 | 1.05 | 2.0 |
| Example 2 | 1.15 | 1.5 |
| Example 3 | 1.1 | 1.6 |
| Example 4 | 1.1 | 1.8 |
| Example 5 | 1.05 | 1.9 |
| Comparative Example 1 | 1.2 | 1.0 |
| Comparative Example 2 | 1.3 | 0.85 |
| Comparative Example 3 | 1.15 | 1.4 |
| Comparative Example 4 | 1.2 | 1.2 |

From the results shown above, it is understood that the Examples are organic electroluminescent devices having longer device lifespan as compared with the Comparative Examples.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An organic electroluminescent device comprising:
   a pair of electrodes including a positive electrode and a negative electrode, at least one of the electrodes being transparent or semi-transparent; and
   an organic compound layer including one or more layers interposed between the pair of electrodes,
   at least one layer included in the organic compound layer containing one or more compounds represented by the following formula (I):

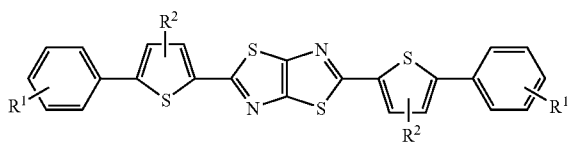

(I)

in formula (I), R¹s each independently representing a linear alkyl group having from 3 to 20 carbon atoms, a linear alkoxy group having from 3 to 20 carbon atoms, a branched alkyl group having from 3 to 20 carbon atoms, or a branched alkoxy group having from 3 to 20 carbon atoms; and R²s each independently representing a hydrogen atom, a linear alkyl group having from 1 to 20 carbon atoms, a linear alkoxy group having from 1 to 20 carbon atoms, a branched alkyl group having from 3 to 20 carbon atoms, or a branched alkoxy group having from 3 to 20 carbon atoms.

2. The organic electroluminescent device of claim 1, wherein R¹s in formula (I) each independently represent a linear substituent having from 3 to 12 carbon atoms, or a branched substituent having from 3 to 12 main chain carbon atoms; and R²s each independently represent a linear substituent having from 1 to 12 carbon atoms, or a branched substituent having from 2 to 12 main chain carbon atoms.

3. The organic electroluminescent device of claim 1, wherein R¹s in formula (I) each independently represent a linear alkyl group having from 3 to 12 carbon atoms, a linear alkoxy group having from 3 to 12 carbon atoms, a branched alkyl group having from 3 to 12 carbon atoms, or a branched alkoxy group having from 3 to 12 carbon atoms.

4. The organic electroluminescent device of claim 1, wherein R²s in formula (I) each independently represent a linear alkyl group having from 1 to 8 carbon atoms, a linear alkoxy group having from 1 to 8 carbon atoms, a branched alkyl group having from 3 to 8 carbon atoms, or a branched alkoxy group having from 3 to 8 carbon atoms.

5. The organic electroluminescent device of claim 1, wherein
the organic compound layer includes at least a light emitting layer, and at least one of an electron transport layer or an electron injection layer, and
at least one layer selected from the light emitting layer, the electron transport layer or the electron injection layer contains one or more compounds represented by formula (I).

6. The organic electroluminescent device of claim 1, wherein
the organic compound layer includes at least a light emitting layer, and at least one of a hole transport layer or a hole injection layer, and
at least one layer selected from the light emitting layer, the hole transport layer or the hole injection layer contains one or more compounds represented by formula (I).

7. The organic electroluminescent device of claim 1, wherein
the organic compound layer includes at least a light emitting layer, at least one of a hole transport layer or a hole injection layer, and at least one of an electron transport layer or an electron injection layer, and
at least one layer selected from the light emitting layer, the hole transport layer, the hole injection layer, the electron transport layer or the electron injection layer contains one or more compounds represented by formula (I).

8. The organic electroluminescent device of claim 1, wherein
the organic compound layer consists of a light emitting layer having charge transport capability, and
the light emitting layer having charge transport capability contains one or more compounds represented by formula (I).

9. The organic electroluminescent device of claim 6, wherein the hole transport layer contains a compound represented by formula (I) and a hole transporting material.

10. The organic electroluminescent device of claim 9, wherein the hole transporting material is selected from the group consisting of a tetraphenylenediamine compound, a triphenylamine compound, a carbazole compound, a stilbene compound, an arylhydrazone compound, and a porphyrin compound.

11. A display medium comprising:
organic electroluminescent devices in at least one of a matrix arrangement or a segment arrangement, each of the organic electroluminescent devices comprising a pair of electrodes including a positive electrode and a negative electrode, at least one of the electrodes being transparent or semi-transparent, and an organic compound layer including one or more layers interposed between the pair of electrodes, at least one layer included in the organic compound layer containing one or more compounds represented by the following formula (I); and
a driving unit that drives the organic electroluminescent devices in at least one of a matrix arrangement or a segment arrangement:

(I)

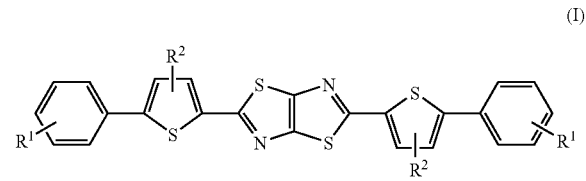

in formula (I), R¹s each independently representing a linear alkyl group having from 3 to 20 carbon atoms, a linear alkoxy group having from 3 to 20 carbon atoms, a branched alkyl group having from 3 to 20 carbon atoms, or a branched alkoxy group having from 3 to 20 carbon atoms; and R²s each independently representing a hydrogen atom, a linear alkyl group having from 1 to 20 carbon atoms, a linear alkoxy group having from 1 to 20 carbon atoms, a branched alkyl group having from 3 to 20 carbon atoms, or a branched alkoxy group having from 3 to 20 carbon atoms.

12. The display medium of claim 11, wherein R¹s in formula (I) each independently represent a linear substituent having from 3 to 12 carbon atoms, or a branched substituent having from 3 to 12 main chain carbon atoms; and R²s each independently represent a linear substituent having from 1 to 12 carbon atoms, or a branched substituent having from 2 to 12 main chain carbon atoms.

13. The display medium of claim 11, wherein R¹ s in formula (I) each independently represent a linear alkyl group having from 3 to 12 carbon atoms, a linear alkoxy group having from 3 to 12 carbon atoms, a branched alkyl group having from 3 to 12 carbon atoms, or a branched alkoxy group having from 3 to 12 carbon atoms.

14. The display medium of claim 11, wherein R²s in formula (I) each independently represent a linear alkyl group having from 1 to 8 carbon atoms, a linear alkoxy group having from 1 to 8 carbon atoms, a branched alkyl group having from 3 to 8 carbon atoms, or a branched alkoxy group having from 3 to 8 carbon atoms.

15. The display medium of claim 11, wherein
the organic compound layer includes at least a light emitting layer, and at least one of an electron transport layer or an electron injection layer, and
at least one layer selected from the light emitting layer, the electron transport layer or the electron injection layer contains one or more compounds represented by formula (I).

16. The display medium of claim 11, wherein
the organic compound layer includes at least a light emitting layer, and at least one of a hole transport layer or a hole injection layer, and
at least one layer selected from the light emitting layer, the hole transport layer or the hole injection layer contains one or more compounds represented by formula (I).

17. The display medium of claim 11, wherein
the organic compound layer includes at least a light emitting layer, at least one of a hole transport layer or a hole injection layer, and at least one of an electron transport layer or an electron injection layer, and
at least one layer selected from the light emitting layer, the hole transport layer, the hole injection layer, the electron transport layer or the electron injection layer contains one or more compounds represented by formula (I).

18. The display medium of claim 11, wherein
the organic compound layer consists of a light emitting layer having charge transport capability, and
the light emitting layer having charge transport capability contains one or more compounds represented by formula (I).

19. A display medium comprising:
a plurality of organic electroluminescent devices of claim 1 in at least one of a matrix arrangement or a segment arrangement; and
a driving unit that drives the plurality of organic electroluminescent devices in at least one of a matrix arrangement or a segment arrangement.

* * * * *